(12) United States Patent
Haick et al.

(10) Patent No.: US 8,999,244 B2
(45) Date of Patent: *Apr. 7, 2015

(54) CHEMICAL SENSORS BASED ON CUBIC NANOPARTICLES CAPPED WITH AN ORGANIC COATING

(75) Inventors: Hossam Haick, Haifa (IL); Ekaterina Dovgolevsky, Haifa (IL)

(73) Assignee: Technion Research and Development Foundation Ltd., Haifa (IL)

( * ) Notice: Subject to any disclaimer, the term of this patent is extended or adjusted under 35 U.S.C. 154(b) by 406 days.

This patent is subject to a terminal disclaimer.

(21) Appl. No.: 12/742,455

(22) PCT Filed: Nov. 20, 2008

(86) PCT No.: PCT/IL2008/001527
§ 371 (c)(1),
(2), (4) Date: May 12, 2010

(87) PCT Pub. No.: WO2009/066293
PCT Pub. Date: May 28, 2009

(65) Prior Publication Data
US 2010/0273665 A1 Oct. 28, 2010

Related U.S. Application Data

(60) Provisional application No. 60/989,130, filed on Nov. 20, 2007.

(51) Int. Cl.
*G01N 21/77* (2006.01)
*B82Y 15/00* (2011.01)
(Continued)

(52) U.S. Cl.
CPC ............... *G01N 21/77* (2013.01); *B82Y 15/00* (2013.01); *B82Y 30/00* (2013.01); *G01N 27/127* (2013.01); *G01N 21/554* (2013.01); *G01N 2021/258* (2013.01)

(58) Field of Classification Search
CPC .... C40B 30/10; G01N 27/126; G01N 27/127; G01N 21/77
USPC .................................................. 422/421, 82.02
See application file for complete search history.

(56) References Cited

U.S. PATENT DOCUMENTS 5,092,218 A   3/1992   Fine
5,109,691 A   5/1992   Corrigan
(Continued)

FOREIGN PATENT DOCUMENTS

EP   1215485   6/2002
EP   1278061   1/2003
(Continued)

OTHER PUBLICATIONS

Ahmadi et al., (1996) "Cubic" Colloidal Platinum Nanoparticles. Chem. Mater. 8(6):1161-3.
(Continued)

*Primary Examiner* — Lore Jarrett
(74) *Attorney, Agent, or Firm* — Roach Brown McCarthy & Gruber, P.C.; Kevin D. McCarthy

(57) ABSTRACT

The present invention provides a sensor apparatus based on 2D films or 3D assemblies of cubic nanoparticles capped with an organic coating. The apparatus is used to determine the composition and preferably measure the concentration of volatile and non-volatile compounds in a sample, with very high sensitivity. Methods for use of the apparatus in applications such as diagnosis of disease, food quality and environmental control are disclosed.

19 Claims, 11 Drawing Sheets

(51) Int. Cl.
*B82Y 30/00* (2011.01)
*G01N 27/12* (2006.01)
*G01N 21/552* (2014.01)
*G01N 21/25* (2006.01)

(56) References Cited

U.S. PATENT DOCUMENTS

| | | | |
|---|---|---|---|
| 5,571,401 | A | 11/1996 | Lewis |
| 5,585,575 | A | 12/1996 | Corrigan |
| 5,698,089 | A | 12/1997 | Lewis |
| 5,801,297 | A | 9/1998 | Mifsud |
| 6,010,616 | A | 1/2000 | Lewis |
| 6,316,268 | B1 | 11/2001 | Yang |
| 6,319,724 | B1 | 11/2001 | Lewis |
| 6,379,622 | B1 | 4/2002 | Polak |
| 6,411,905 | B1 | 6/2002 | Guoliang |
| 6,467,333 | B2 | 10/2002 | Lewis |
| 6,537,498 | B1 | 3/2003 | Lewis |
| 6,541,617 | B1 | 4/2003 | Bamdad |
| 6,571,649 | B2 | 6/2003 | Sakairi |
| 6,606,566 | B1 | 8/2003 | Sunshine |
| 6,609,068 | B2 | 8/2003 | Cranley |
| 6,620,109 | B2 | 9/2003 | Hanson, III |
| 6,746,960 | B2 | 6/2004 | Goodman |
| 6,759,010 | B2 | 7/2004 | Lewis |
| 6,767,732 | B2 | 7/2004 | Alocilja |
| 6,773,926 | B1 | 8/2004 | Freund |
| 6,820,012 | B2 | 11/2004 | Sunshine |
| 6,839,636 | B1 | 1/2005 | Sunshine |
| 6,840,120 | B2 | 1/2005 | Sakairi |
| 6,841,391 | B2 | 1/2005 | Lewis |
| 6,872,786 | B2 | 3/2005 | Murray |
| 7,034,677 | B2 | 4/2006 | Steinthal |
| 7,052,854 | B2 | 5/2006 | Melker |
| 7,144,553 | B2 | 12/2006 | Lewis |
| 7,171,312 | B2 | 1/2007 | Steinthal |
| 7,186,381 | B2 | 3/2007 | Penner |
| 7,224,345 | B2 | 5/2007 | Kawell |
| 7,482,067 | B2 | 1/2009 | Sohn |
| 2003/0159927 | A1 | 8/2003 | Lewis |
| 2003/0198956 | A1* | 10/2003 | Makowski et al. ............ 435/6 |
| 2004/0033165 | A1 | 2/2004 | Lewis |
| 2004/0204915 | A1 | 10/2004 | Steinthal |
| 2005/0150778 | A1 | 7/2005 | Lewis |
| 2005/0241935 | A1 | 11/2005 | Lewis |
| 2005/0263394 | A1 | 12/2005 | Lewis |
| 2006/0034731 | A1 | 2/2006 | Lewis |
| 2006/0040318 | A1* | 2/2006 | Melker et al. ............ 435/7.1 |
| 2006/0160134 | A1 | 7/2006 | Melker |
| 2007/0059211 | A1 | 3/2007 | Edmiston |
| 2007/0114138 | A1 | 5/2007 | Krasteva |
| 2007/0127164 | A1 | 6/2007 | Ofek |
| 2007/0132043 | A1 | 6/2007 | Bradley |
| 2007/0165217 | A1 | 7/2007 | Johansson |
| 2007/0231790 | A1 | 10/2007 | Su |
| 2007/0264719 | A1 | 11/2007 | Santra |
| 2008/0077331 | A1 | 3/2008 | Lewis |
| 2011/0015872 | A1* | 1/2011 | Haick et al. ............ 702/23 |

FOREIGN PATENT DOCUMENTS

| | | | |
|---|---|---|---|
| FR | 2783051 | 3/2000 | |
| WO | 99/27357 | 6/1999 | |
| WO | 00/00808 | 1/2000 | |
| WO | 2005/059952 | 6/2005 | |
| WO | WO2006131400 A1 * | 12/2006 | ............ G01N 21/55 |

OTHER PUBLICATIONS

Chen et al., Ellipsometrically probed plasmonic resonances in a square array of Au nanocubes. CLEO '07. 2007 Conference on Lasers and Electro-Optics May 5-11, 2007 Baltimore, MD, USA, Piscataway, NJ, USA, May 1, 2007, pp. 1-2.
Dovgolevsky & Haick, (2008) Direct observation of the transition point between quasi-spherical and cubic nanoparticles in a two-step seed-mediated growth method. Small, 4(11):2059-66.
Evans et al., (2000) Vapour sensing using hybrid organic-inorganic nanostructured materials. J. Mater. Chem., 10(1):183-8.
Joseph et al., (2008) Gold Nanoparticle/Organic Networks as Chemiresistor Coatings: The Effect of Film Morphology on Vapor Sensitivity. J. Phys. Chem. C, 112(32):12507-14.
Li D.G. et al., (2004) Simple method for preparation of cubic Ag nanoparticles and their self-assembled films. Thin Solid Films 460(1-2):78-82.
Lisiecki, (2005) Size, shape, and structural control of metallic nanocrystals. J. Phys. Chem. B, 109(25):12231-44.
Narayanan & El-Sayed, (2003) Effect of Catalytic Activity on the Metallic Nanoparticle Size Distribution: Electron-Transfer Reaction between Fe(CN)6 and Thiosulfate Ions Catalyzed by PVP-Platinum Nanoparticles. J. Phys. Chem. B, 107(45):12416-24.
Narayanan & El-Sayed, (2004) Effect of Nanocatalysis in Colloidal Solution on the Tetrahedral and Cubic Nanoparticle Shape: Electron-Transfer Reaction Catalyzed by Platinum Nanoparticles. J. Phys. Chem. B, 108(18):5726-33.
Sau & Murphy, (2004) Room temperature, high-yield synthesis of multiple shapes of gold nanoparticles in aqueous solution. J. Am. Chem. Soc. 126(28):8648-9.
Sherry L.J. et al., (2005) Localized surface plasmon resonance spectroscopy of single silver nanocubes. Nano Lett Am Chem Soc USA 5(10):2034-8.
Shukla et al., (2007) Synthesis and self-assembly of magnetic nanoparticles. Surface Science 601(13):2615-7.
Sirbuly D.J. et al., (2007) Multifunctional nanowire evanescent wave optical sensors. Adv Mater 19(1):61-6.
Sun & Xia, (2003) Gold and silver nanoparticles: a class of chromophores with colors tunable in the range from 400 to 750 nm. The Analyst 128(6):686-91.
Wohltjen & Snow, (1998) Colloidal Metal-Insulator-Metal Ensemble Chemiresistor Sensor. Anal. Chem., 70(14):2856-9.
Xiangfeng et al., (2007) The preparation and gas-sensing properties of NiFe2O4 nanocubes and nanorods. Sensors and Actuators B, 123(2):793-7.
Zhao et al., (1997) Soft lithographic methods for nano-fabrication. J. Mater. Chem. 7(7):1069-74.
Wiley et al., Shape-Controlled Synthesis of Metal Nanostructures: The Case of Silver; Chem. Eur. J. 2005, 11, 454-463—10 pages.
Ahmadi et al., (1996) "Cubic" Colloidal Platinum Nanoparticles. Chem Mater 8: 1161-1163.
Dovgolevsky and Haick (2008) Direct Observation of the Transition Point between Quasi-Spherical and Cubic Nanoparticles in Two-Step Seed-Mediated Growth Method. Small 4(11): 2059-66.
Dovgolevsky et al., (2009) Chemically sensitive resistors based on monolayer-capped cubic nanoparticles: towards configurable nanoporous sensors. Small 5(10): 1158-1161.
Haick (2007) Chemical sensors based on molecularly modified metallic nanoparticles. Journal of Physics D: Applied Physics 40 (23): 7173-7186.
Han et al., (2005) Nanoparticle-structured sensing array materials and pattern recognition for VOC detection. Sensors and Actuators B 106(1): 431-441.
Sau and Murphy (2004) Room Temperature, High-Yield Synthesis of Multiple Shapes of Gold Nanoparticles in Aqueous Solution. J Am Chem Soc 126: 8648-8649.
Wang (2004) Microchip devices for detecting terrorist weapons. Analytica Chimica Acta 507: 3-10.

* cited by examiner

Figure 3A
Figure 3B
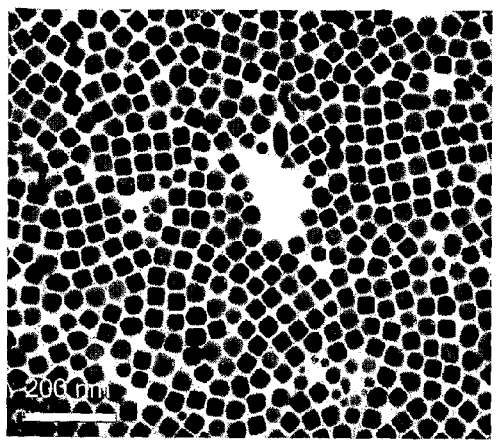 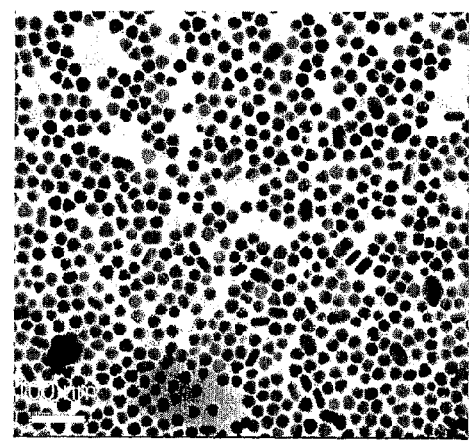

CHEMICAL SENSORS BASED ON CUBIC NANOPARTICLES CAPPED WITH AN ORGANIC COATING

REFERENCE TO CO-PENDING APPLICATIONS

Priority is claimed as a U.S. national entry under 35 U.S.C. 371 of PCT/IL2008/001527, filed on Nov. 20, 2008, which claims priority to U.S. provisional patent application No. 60/989,130, filed on Nov. 20, 2007.

FIELD OF THE INVENTION

The present invention relates to an apparatus comprising sensors of cubic nanoparticles capped with an organic coating for detecting minute concentrations of volatile and non-volatile compounds with very high sensitivity. The invention further provides methods of use thereof in identifying various disease biomarkers, and in food quality and environmental control.

BACKGROUND OF THE INVENTION

Metal nanoparticles constitute an intermediate state between bulk materials and atomic or molecular structures. In contrast to bulk metals, which display constant physical properties regardless of their size, the properties of nanoparticles are highly dependent on their size. This size dependency is attributed to the nature of the nanoparticles, having a discrete and quantized energy spectrum. Obeying quantum-mechanical rules, their electronic structures differ from those of bulk metal on one hand, and of molecular compounds on the other.

The characteristics of nanoparticles stem from various features such as particle size, shape and inter-particle distance. A particularly important feature is their surface to bulk ratio since the percentage of atoms at the surface increases significantly as the size of the material approaches the nanoscale. Furthermore, molecules that are attached to the surface play a key role in determining the physical and chemical properties of these particles. They are particularly important for their stabilization and are often referred to as organic coating.

The application of organic coating on nanoparticles has several functionalities. It modifies the chemical characteristics of "bare" nanoparticles and, most importantly, affects their electronic properties. Furthermore, it is also possible to obtain electron transport between the nanoparticles and the organic coating thus introducing cooperative effects. Nanoparticles capped with an organic coating (NPCOC) are therefore of high technological importance, particularly since there is a wide variety of compounds from which both the nanoparticles and their organic coating may be selected. Furthermore, the organic coating can be tailor-made in order to control the chemical and physical properties of the nanoparticles, in a qualitative as well as quantitative manner, to enhance desired properties of the NPCOCs including solubility, stability, etc.

The use of NPCOCs for sensing applications has many advantages. The sensing signal from an NPCOC sensing device can be easily obtained either by controlled aggregation (self-assembly) or by swelling of the NPCOC mainly through hydrogen-bonding. Other interactions, including $\pi$-$\pi$, van-der-Waals, electrostatic, charge-transfer, host-guest or antigen-antibody, may also contribute to sensing. Additionally, parameters which include, for instance, nanoparticles and/or aggregate size, inter-particle distance, composition, periodicity, and aggregate thermal stability can be manipulated in order to enhance the sensing signal. Enhanced selectivity can further be achieved through modifying the binding characteristics of the capping film as well as linker molecules. The morphology and thickness of NPCOC networks were shown to induce a dramatic influence on sensor response, wherein changes in permittivity induced a decrease in resistance of NPCOC thinner films (Joseph et al., *J. Phys. Chem. C*, 112, 12507, 2008).

Another advantage for the use of NPCOCs for sensing applications is increased sensitivity. This is mainly attributed to the three dimensional assembly of structures which provide a framework for signal amplifications. Other advantages stem from the coupling of nano-structures to solid-state substrates, thus providing easy array integration, rapid responses, and low power-driven portable format.

Chemical sensors based on NPCOCs can be fabricated as electronic nose devices. Such devices perform odor detection through the use of an array of cross-reactive sensors in conjunction with pattern recognition methods. In contrast to the "lock-and-key" model, each sensor in the electronic nose device is widely responsive to a variety of odorants. In this architecture, each analyte produces a distinct fingerprint from an array of broadly cross-reactive sensors. This configuration may be used to considerably widen the variety of compounds to which a given matrix is sensitive, to increase the degree of component identification and, in specific cases, to perform an analysis of individual components in complex multi-component (bio) chemical media. Pattern recognition algorithms can then be applied to the entire set of signals, obtained simultaneously from all the sensors in the array, in order to glean information on the identity, properties and concentration of the vapor exposed to the sensor array.

Sensors based on changes in the physical and/or electrical properties of films composed of spherical NPCOC ("SNP-COC") were applied as chemiresistors, quartz crystal microbalance, electrochemical sensors and the like. Some examples for the use of SNPCOCs for sensing applications are disclosed in U.S. Pat. Nos. 5,571,401, 5,698,089, 6,010,616, 6,537,498; Patent Application Nos. WO 99/27357, WO 00/00808, FR 2,783,051 US 2007/0114138; and in Wohltjen et al. (*Anal. Chem.*, 70, 2856, 1998), and Evans et al. (*J. Mater. Chem.*, 8, 183, 2000).

U.S. Pat. No. 6,773,926 discloses sensors and sensor systems for detecting analytes in fluids, the sensors include a plurality of particles having one or more capping ligands coupled to a metallic core. Exposure of the sensors to a fluid containing a chemical analyte causes the analyte to react with the metal core, preferably by displacing one or more of the capping ligands. The chemical analyte can be detected through a change in electrical or optical properties of the sensors.

U.S. Pat. No. 6,746,960 is directed to techniques for detecting and identifying analytes in fluids. The system used therein comprises an insulating layer covering a conductive layer on a substrate. A sensor well comprising a sensor material whose electrical properties are changed in the presence of an analyte is patterned and etched in the insulating and conductive layers to enable analyte detection.

U.S. Pat. No. 7,052,854 discloses systems and methods for ex vivo diagnostic analysis using nanostructure-based assemblies comprising a nanoparticle, a means for detecting a target analyte/biomarker, and a surrogate marker. The sensor technology is based on the detection of the surrogate marker which indicates the presence of the target analyte/biomarker in a sample of a bodily fluid.

EP 1,215,485 discloses chemical sensors comprising a nanoparticle film formed on a substrate, the nanoparticle film comprising a nanoparticle network interlinked through linker molecules having at least two linker units. The linker units are capable of binding to the surface of the nanoparticles and at least one selectivity-enhancing unit having a binding site for reversibly binding an analyte molecule. A change of a physical property of the nanoparticle film is detected through a detection means.

Theoretical as well as experimental observations indicate that SNPCOC based sensors are typically limited to detecting analytes in a concentration range of 100-1000 parts per billion (ppb). This limitation has been attributed to two main reasons. First, while voids between adjacent (spherical) nanoparticles can host analyte molecules during the exposure process, they do not contribute to the obtained sensing signal. Second, the contact interface between adjacent spherical nanoparticles, onto which analyte molecules adsorb and induce sensing signals (e.g., by inducing swelling/aggregation of the film), is limited to a very small area in comparison to the total surface area of the SNPCOCs.

For the reasons mentioned hereinabove, obtaining high sensing performance requires an increase in film thickness. However, such an increase results in intensified diffusion limitations, thus reducing the response time. Hence, there is an unmet need for fast responsive sensors having improved sensitivity as well as selectivity. Furthermore, there is an unmet need for a reliable sensing apparatus to analyze either volatile or non-volatile compounds.

SUMMARY OF THE INVENTION

The present invention provides a sensing apparatus for detecting volatile and non-volatile compounds with very high sensitivity. The apparatus comprises sensors of cubic nanoparticles capped with an organic coating. The present invention further provides a system comprising an apparatus having an array of chemically sensitive sensors of cubic nanoparticles capped with an organic coating in conjunction with a learning and pattern recognition analyzer, wherein said learning and pattern recognition analyzer receives sensor output signals and compares them to stored data.

The invention is based in part on the unexpected finding that cubic nanoparticles capped with organic molecules can be used as sensors with improved sensitivity as compared to spherical nanoparticles capped with an organic coating. It was not previously realized that the disadvantages of known configurations could be overcome by utilizing cubic nanoparticles instead of spherical nanoparticles or nanoparticles of other geometries. The advantage of using cubic nanoparticles stems from the low fraction of voids in 2D or 3D structure assemblies, and from the increased interface contacts between adjacent conductive particles as compared to particles having spherical geometry. The increase in interface contacts enhances the efficacy of electron transfer to provide improved signal to noise ratios. Increased sensitivity is further induced by the cubic geometry through the vertexes/edges of cubic nanoparticles which exhibit higher field effects than smooth geometries.

According to one aspect, the present invention provides an apparatus comprising at least one chemically sensitive sensor for the detection of volatile and non-volatile compounds, wherein the chemically sensitive sensor comprises cubic nanoparticles capped with an organic coating. In one embodiment, the nanoparticles comprise a conductive core capped with an organic coating comprising a monolayer or multilayers of organic compounds, wherein the organic compounds are selected from small molecules, monomers, oligomers and polymers.

According to another aspect, the present invention provides a system for detecting volatile and non-volatile compounds comprising an apparatus comprising an array of chemically sensitive sensors of cubic nanoparticles capped with an organic coating, and a learning and pattern recognition analyzer wherein said learning and pattern recognition analyzer receives sensor signal outputs and compares them to stored data.

According to one embodiment, the apparatus and system of the present invention detect volatile and non-volatile compounds with sensitivity of less than one part per million (ppm). According to another embodiment, the apparatus and system of the present invention detect volatile and non-volatile compounds with sensitivity of less than 100 parts per billion (ppb). According to yet another embodiment, the apparatus and system of the present invention detect volatile and non-volatile compounds with sensitivity of less than 10 parts per billion (ppb).

In some embodiments, the apparatus and system disclosed herein comprise conductive cubic nanoparticle cores selected from metals and metal alloys. According to certain embodiments, the nanoparticle conductive cores comprise metals and metal alloys selected from the group consisting of Au, Ag, Ni, Co, Pt, Pd, Cu, Al, Au/Ag, Au/Cu, Au/Ag/Cu, Au/Pt, Au/Pd, Au/Ag/Cu/Pd, Pt—Rh, Ni—Co, and Pt—Ni—Fe.

In various embodiments, the coating of the conductive nanoparticle cores comprises a monolayer or multilayers of organic compounds, wherein the organic compounds can be small molecules, monomers, oligomers or polymers. In particular embodiments, the organic compounds are selected from the group consisting of alkylthiols, arylthiols, alkylarylthiols, alkylthiolates, ω-functionalized alkylthiolates, arenethiolates, (γ-mercaptopropyl)tri-methyloxysilane, dialkyl sulfides, diaryl sulfides, alkylaryl sulfides, dialkyl disulfides, diaryl disulfides, alkylaryl disulfides, alkyl sulfites, aryl sulfites, alkylaryl sulfites, alkyl sulfates, aryl sulfates, alkylaryl sulfates, xanthates, oligonucleotides, polynucleotides, dithiocarbamate, alkyl amines, aryl amines, diaryl amines, dialkyl amines, alkylaryl amines, arene amines, alkyl phosphines, aryl phosphines, dialkyl phosphines, diaryl phosphines, alkylaryl phosphines, phosphine oxides, alkyl carboxylates, aryl carboxylates, dialkyl carboxylates, diaryl carboxylates, alkylaryl carboxylates, cyanates, isocyanates, peptides, proteins, enzymes, polysaccharides, phospholipids, and combinations and derivatives thereof. In a currently preferred embodiment, the organic coating comprises alkylthiols with $C_3$-$C_{24}$ chains.

In certain embodiments, the sensing apparatus and system of the present invention comprise cubic nanoparticles capped with an organic coating in a configuration selected from the group consisting of 1D wires, 2D films, and 3D assemblies.

In some embodiments, the sensing apparatus and system of the present invention comprise sensors comprising a plurality of cubic nanoparticles capped with an organic coating, and further comprising at least one of a chemiresistor, chemicapacitor, quartz crystal microbalance, bulk acoustic wave (BAW) and surface acoustic wave (SAW) resonator, electrochemical cell, surface plasmon resonance (SPR), and optical spectroscopy.

Without being bound by any theory or mechanism of action, it is contemplated that sensing occurs via aggregation or swelling of the cubic nanoparticles capped with an organic coating assemblies, through hydrogen-bonding, π-π, host-guest, van der Waals, electrostatic, charge-transfer or antigen-antibody interactions. In another embodiment, sensing occurs via changing of permittivity upon analyte sorption.

According to another aspect, the system of the present invention comprises an apparatus for detecting volatile and non-volatile compounds comprising an array of chemically sensitive sensors of cubic nanoparticles capped with an organic coating, in conjunction with a learning and pattern recognition analyzer, wherein the learning and pattern recognition analyzer receives sensor output signals and compares them to stored data. The learning and pattern recognition analyzer utilizes various algorithms including, but not limited to, artificial neural networks, multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART) and statistical methods including, but not limited to, principal component analysis (PCA), partial least squares (PLS), multiple linear regression (MLR), principal component regression (PCR), discriminant function analysis (DFA) including linear discriminant analysis (LDA), and cluster analysis including nearest neighbor.

According to yet another aspect, the present invention provides a method of determining at least one of the composition and concentration of selected compounds in a sample using the system of the present invention, comprising the steps of: (a) providing a system comprising an apparatus for detecting volatile and non-volatile compounds comprising an array of chemically sensitive sensors of cubic nanoparticles capped with an organic coating, and a learning and pattern recognition analyzer, wherein the learning and pattern recognition analyzer receives sensor output signals and compares them to stored data, (b) exposing the sensor array of the apparatus to the sample, and (c) using learning and pattern recognition algorithms to detect the presence of volatile and non-volatile compounds and preferably measure their concentration in the sample.

In particular embodiments, the method of determining at least one of the composition and concentration of selected compounds in a sample comprises measuring a change in any one or more of conductivity, resistance, impedance, capacitance, inductance, or optical properties of the sensors upon exposure to volatile and non-volatile compounds to be detected. In a currently preferred embodiment, the method of determining at least one of the composition and concentration of selected compounds in a sample comprises detecting volatile and non-volatile compounds through spectroscopic ellipsometry.

According to various embodiments, the present invention provides a method for diagnosing a disease in a subject by determining at least one of the composition and concentration of disease biomarkers in a sample, comprising the steps of: (a) collecting a sample suspected of containing volatile and non-volatile compounds, wherein the sample is selected from exhaled breath and at least one bodily fluid or secretion of the subject, (b) providing a system comprising an apparatus comprising an array of chemically sensitive sensors of cubic nanoparticles capped with an organic coating, and a learning and pattern recognition analyzer, wherein said learning and pattern recognition analyzer receives sensor output signals and compares them to stored data, (c) exposing the sensor array of the apparatus to the sample, and (d) using learning and pattern recognition algorithms to determine the composition and preferably measure the concentration of selected compounds indicative of a disease in the sample.

In certain aspects, the present invention relates to the use of a system comprising an apparatus comprising an array of chemically sensitive sensors of cubic nanoparticles capped with an organic coating and a learning and pattern recognition analyzer, wherein the learning and pattern recognition analyzer receives sensor output signals and compares them to stored data, for the preparation of a sensing device for detecting volatile and non-volatile compounds. In a currently preferred embodiment, the use disclosed herein is designated towards detecting volatile and non-volatile compounds indicative of a disease in a subject comprising exposing the sensor array of the apparatus to a sample selected from exhaled breath and at least one bodily fluid or secretion of the subject, and using learning and pattern recognition algorithms to determine any one of the composition and concentration of selected disease biomarkers.

The present invention further provides a system comprising an apparatus comprising an array of chemically sensitive sensors of cubic nanoparticles capped with an organic coating, and a learning and pattern recognition analyzer for diagnosing a disease in a subject comprising the steps of: (a) exposing the sensor array of the apparatus to a sample of at least one bodily fluid or secretion, and (b) using learning and pattern recognition algorithms to determine the composition and preferably measure the concentration of selected compounds indicative of a disease in the sample.

Encompassed within the scope of the present invention is the diagnosis of various diseases including, but not limited to, cancer, acute asthma, hepatic encephalopathy, rheumatoid arthritis, renal failure, schizophrenia, ketosis, cardiopulmonary disease, uremia, diabetes mellitus, dysgeusia/dysosmia, cystinuria, cirrhosis, histidinemia, tyrosinemia, halitosis and phenylketonuria. According to currently preferred embodiments, the present invention provides a method for differentiating between patients with different types of cancer.

Bodily fluids or secretions that can be tested according to the principles of the present invention include, but are not limited to, serum, urine, feces, sweat, vaginal discharge, saliva and sperm.

According to certain embodiments, the present invention provides methods for identifying or characterizing spoilage in food products via the determination of at least one of the composition and concentration of volatile and non-volatile compounds in a food sample, comprising the steps of: (a) collecting a sample of food product, (b) providing a system comprising an apparatus for detecting volatile and non-volatile compounds comprising an array of chemically sensitive sensors of cubic nanoparticles capped with an organic coating, and a learning and pattern recognition analyzer, wherein said learning and pattern recognition analyzer receives sensor output signals and compares them to stored data, (c) exposing the sensor array of the apparatus to the sample, and (d) using learning and pattern recognition algorithms to determine the composition and preferably measure the concentration of selected compounds indicative of food spoilage.

In some embodiments, the present invention provides the use of a system comprising an apparatus comprising an array of chemically sensitive sensors of cubic nanoparticles capped with an organic coating, and a learning and pattern recognition analyzer, wherein the learning and pattern recognition analyzer receives sensor output signals and compares them to stored data, for detecting spoilage in food products via the determination of at least one of the composition and concentration of volatile and non-volatile compounds indicative of spoilage in the sample.

The present invention further provides a method for detecting pollutants in water or air for environmental monitoring, comprising the steps of: (a) collecting a sample of water or air to a container, (b) providing a system comprising an apparatus comprising an array of chemically sensitive sensors of cubic nanoparticles capped with an organic coating, and a learning and pattern recognition analyzer, wherein the learning and pattern recognition analyzer receives sensor output signals and compares them to stored data, (c) exposing the sensor array of the apparatus to the sample, and (d) using learning and pattern recognition algorithms to determine the composition and preferably measure the concentration of volatile and non-volatile compounds indicative of environmental pollution. In some embodiments, the present invention provides the use of a system comprising an apparatus comprising an array of chemically sensitive sensors of cubic nanoparticles capped with an organic coating, and a learning and pattern recognition analyzer, wherein the learning and pattern recognition analyzer receives sensor output signals and compares them to stored data, for environmental monitoring comprising determining at least one of the composition and concentration of volatile and non-volatile compounds indicative of water or air pollution.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE FIGURES

FIGS. 3A-3B. Transmission electron micrographs of cubic (3A) and spherical (3B) gold nanoparticles.

DETAILED DESCRIPTION OF THE INVENTION

The present invention provides an apparatus comprising 1D wires, 2D films or 3D assemblies of cubic nanoparticles capped with an organic coating (cubic NPCOC) as chemically sensitive sensors. The apparatus of the present invention is designed for detecting volatile and non-volatile compounds in gases, vapors and/or liquids with very high sensitivity. The present invention further provides a system comprising an array of sensors of cubic nanoparticles capped with an organic coating and a learning and pattern recognition analyzer which utilizes neural network algorithms for detecting and classifying certain volatile and non-volatile compounds. Further disclosed are methods of use thereof in detecting certain biomarkers for diagnostic and prognostic purposes.

Figure 1A:
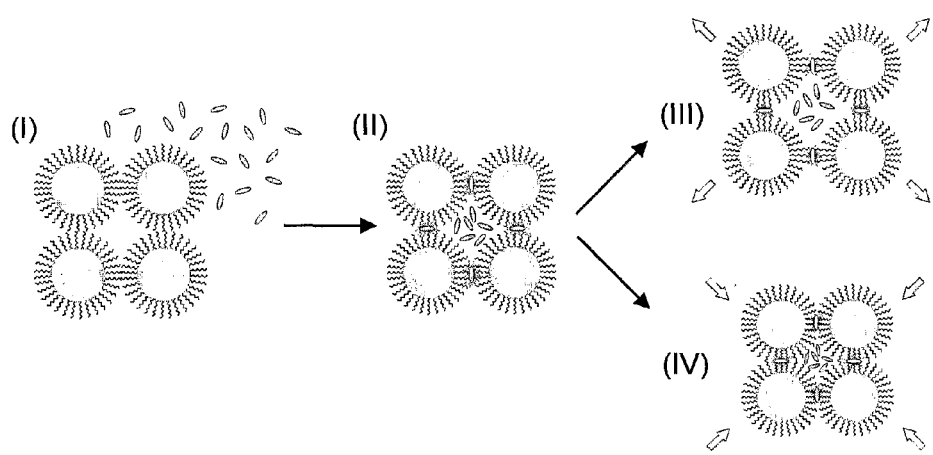
FIG. 1A. Schematic illustration of the swelling- (or aggregation)-based sensing mechanism for films/assemblies of molecularly modified spherical nanoparticles (SNPCOC). (I) before analyte adsorption, (II) after analyte adsorption, (III) swelling following analyte adsorption, or (IV) aggregation following analyte adsorption.
Figure 1B:
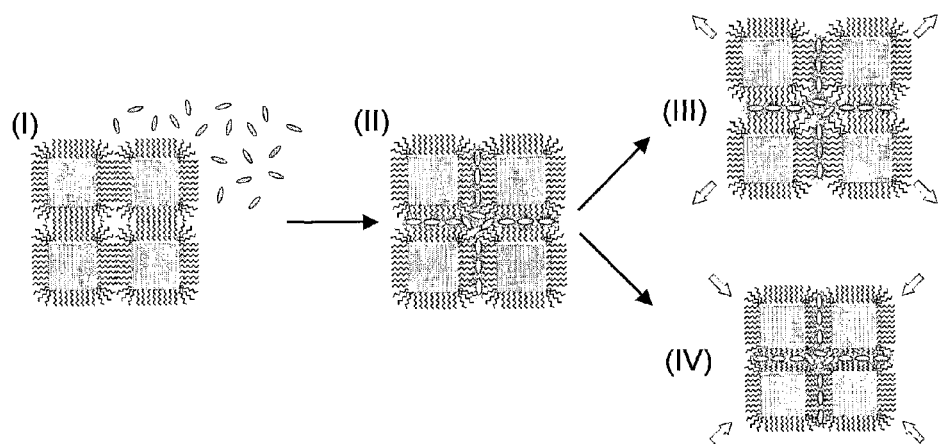
FIG. 1B. Schematic illustration of the swelling- (or aggregation)-based sensing mechanism for films/assemblies of molecularly modified cubic nanoparticles capped with an organic coating. (I) before analyte adsorption, (II) after analyte adsorption, (III) swelling following analyte adsorption, or (IV) aggregation following analyte adsorption.

Upon adsorption of an analyte, the film/assembly of cubic NPCOCs can either swell, or aggregate (FIG. 1B (III) and (IV), respectively). In thin films of NPCOCs a relative change in the permittivity constant of the film upon analyte adsorption may be generated. The response introduced upon analyte exposure is determined by the nature of the interaction between analyte species and the molecular coating of the nanoparticles. As illustrated in FIGS. 1A-1B, only molecules at the interface between molecularly modified nanoparticles contribute to the swelling/aggregation. On the contrary, molecules that occupy the voids between adjacent nanoparticles, contribute little or none to the total swelling of the film. The contact interface between adjacent cubic NPCOCs, where sorption of analyte molecules induces sensing signals, is significantly larger than the contact interface of equivalent spherical nanoparticles. Therefore, a film of molecularly modified cubic nanoparticles requires a lower concentration of analytes to induce a given swelling/aggregation, as compared to equivalent films based on molecularly modified spherical nanoparticles. Furthermore, the larger interface between adjacent conductive nanoparticles in cubic NPCOCs in comparison to SNPCOCs, results in an increase of the electron tunneling/hopping efficiency from one nanoparticle to another, hence lowering the background noise. Films/assemblies composed of cubic nanoparticles are thus more efficient and consequently more sensitive, in comparison to equivalent films of spherical nanoparticles (SNPCOCs).

Another important feature of cubic NPCOCs stems from structural considerations. The vertexes/edges of cubic nanoparticles exhibit higher field effects than the center of the cubic facets. It is therefore advantageous that NPCOCs will exhibit structures having non-uniform field effects on their surface contradictory to SNPCOCs which exhibit a more uniform and smooth surfaces.

Similar to olfactory receptors, increased sensitivity and rate of response of chemical sensors is typically achieved by reducing the dimensions of the sensing apparatus. Cubic NPCOC sensors are thus more sensitive, more controlled, and more suitable to differentiate between subtle differences in mixtures of volatile and/or non-volatile compounds, than films/assemblies of SNPCOC.

In one embodiment, the apparatus comprising sensors of cubic NPCOCs comprises nanoparticle conductive cores capped with non-conductive organic molecules. As used herein the terms "cubic NP" or "cubic nanoparticles" may be used interchangeably, and are defined as three-dimensional solid particles, wherein each particle substantially comprises six faces, facets or sides, wherein three faces, facets or sides essentially meet at a single vertex. Alternatively each three faces, facets or sides meet a joined surface. The dimensions of a given facet range between about 0.1 to about 150 nm, and more preferably between about 1 to about 80 nm. In some embodiments, the term cubic nanoparticles refers to a population of nanoparticles wherein at least 50% of the particles exhibit cubic morphology. More preferably, the term cubic nanoparticles refers to a population of nanoparticles wherein at least 70% of the particles exhibit cubic morphology. Most preferably, the term cubic nanoparticles refers to a population of nanoparticles wherein at least 90% of the particles exhibit cubic morphology.

As used herein the terms "cubic NP" or "cubic nanoparticles" may also refer to nanoparticles each having 4-20 preferably 5-14 faces, facets or sides, wherein six of the faces, facets or sides comprise more than 40%, preferably more than 60%, most preferably more than 80% of the nanoparticle surface.

According to certain embodiments, the cubic nanoparticles comprise conductive metal cores. In other embodiments, the cubic nanoparticles comprise conductive metal alloy cores. Suitable non-limiting examples are metals of Au, Ag, Ni, Co, Pt, Pd, Cu, Al; and metal alloys of Au/Ag, Au/Cu, Au/Ag/Cu, Au/Pt, Au/Pd, Au/Ag/Cu/Pd, Pt—Rh, Ni—Co, and Pt—Ni—Fe.

The coating of the conductive nanoparticle cores comprises a monolayer or multilayers of organic compounds, wherein the organic compounds can be small molecules, monomers, oligomers or polymers. In particular embodiments, the organic compounds are selected from the group consisting of alkylthiols, e.g., alkylthiols with $C_3$-$C_{24}$ chains, arylthiols, alkylarylthiols, alkylthiolates, ω-functionalized alkylthiolates, arenethiolates, (γ-mercaptopropyl)tri-methyloxysilane, dialkyl sulfides, diaryl sulfides, alkylaryl sulfides, dialkyl disulfides, diaryl disulfides, alkylaryl disulfides, alkyl sulfites, aryl sulfites, alkylaryl sulfites, alkyl sulfates, aryl sulfates, alkylaryl sulfates, xanthates, oligonucleotides, polynucleotides, dithiocarbamate, alkyl amines, aryl amines, diaryl amines, dialkyl amines, alkylaryl amines, arene amines, alkyl phosphines, dialkyl phosphines, aryl phosphines, diaryl phosphines, alkylaryl phosphines, dialkyl phosphines, diaryl phosphines, alkylaryl phosphines, phosphine oxides, alkyl carboxylates, aryl carboxylates, dialkyl carboxylates, diaryl carboxylates, alkylaryl carboxylates, dialkyl carboxylates, diaryl carboxylates, alkylaryl carboxylates, cyanates, isocyanates, peptides, proteins, enzymes, polysaccharides, phospholipids, and combinations and derivatives thereof.

Other organic compounds suitable as capping agents include, but are not limited to, alkenyl thiols, alkynyl thiols, cycloalkyl thiols, heterocyclyl thiols, heteroaryl thiols, alkenyl thiolates, alkynyl thiolates, cycloalkyl thiolates, heterocyclyl thiolates, heteroaryl thiolates, alkenyl sulfides, alkynyl sulfides, cycloalkyl sulfides, heterocyclyl sulfides, heteroaryl sulfides, alkenyl disulfides, alkynyl disulfides, cycloalkyl disulfides, heterocyclyl disulfides, heteroaryl disulfides, alkenyl sulfites, alkynyl sulfites, cycloalkyl sulfites, heterocyclyl sulfites, heteroaryl sulfites, alkenyl sulfates, alkynyl sulfates, cycloalkyl sulfates, heterocyclyl sulfates, heteroaryl sulfates, alkenyl amines, alkynyl amines, cycloalkyl amines, heterocyclyl amines, heteroaryl amines, alkenyl carboxylates, alkynyl carboxylates, cycloalkyl carboxylates, heterocyclyl carboxylates, heteroaryl carboxylates.

An "alkyl" group refers to a saturated aliphatic hydrocarbon, including straight-chain, branched-chain and cyclic alkyl groups. In one embodiment, the alkyl group has 1-12 carbons designated here as $C_1$-$C_{12}$-alkyl. In another embodiment, the alkyl group has 2-6 carbons designated here as $C_2$-$C_6$-alkyl. In another embodiment, the alkyl group has 2-4 carbons designated here as $C_2$-$C_4$-alkyl. In a currently preferred embodiment, the alkyl group has 3-24 carbons designated here as $C_3$-$C_{24}$ alkyl. The alkyl group may be unsubstituted or substituted by one or more groups selected from halogen, haloalkyl, acyl, amido, ester, cyano, nitro, and azido.

A "cycloalkyl" group refers to a non-aromatic mono- or multicyclic ring system. In one embodiment, the cycloalkyl group has 3-10 carbon atoms. In another embodiment, the cycloalkyl group has 5-10 carbon atoms. Exemplary monocyclic cycloalkyl groups include cyclopentyl, cyclohexyl, cycloheptyl and the like. An alkylcycloalkyl is an alkyl group as defined herein bonded to a cycloalkyl group as defined herein. The cycloalkyl group can be unsubstituted or substituted with any one or more of the substituents defined above for alkyl.

An "alkenyl" group refers to an aliphatic hydrocarbon group containing at least one carbon-carbon double bond including straight-chain, branched-chain and cyclic alkenyl groups. In one embodiment, the alkenyl group has 2-8 carbon atoms (a $C_{2-8}$ alkenyl). In another embodiment, the alkenyl group has 2-4 carbon atoms in the chain (a $C_{2-4}$ alkenyl). Exemplary alkenyl groups include ethenyl, propenyl, n-butenyl, i-butenyl, 3-methylbut-2-enyl, n-pentenyl, heptenyl, octenyl, cyclohexyl-butenyl and decenyl. An alkylalkenyl is an alkyl group as defined herein bonded to an alkenyl group as defined herein. The alkenyl group can be unsubstituted or substituted through available carbon atoms with one or more groups defined hereinabove for alkyl.

An "alkynyl" group refers to an aliphatic hydrocarbon group containing at least one carbon-carbon triple bond including straight-chain and branched-chain. In one embodiment, the alkynyl group has 2-8 carbon atoms in the chain (a $C_{2-8}$ alkynyl). In another embodiment, the alkynyl group has 2-4 carbon atoms in the chain (a $C_{2-4}$ alkynyl). Exemplary alkynyl groups include ethynyl, propynyl, n-butynyl, 2-butynyl, 3-methylbutynyl, n-pentynyl, heptynyl, octynyl and decynyl. An alkylalkynyl is an alkyl group as defined herein bonded to an alkynyl group as defined herein. The alkynyl group can be unsubstituted or substituted through available carbon atoms with one or more groups defined hereinabove for alkyl.

An "aryl" group refers to an aromatic monocyclic or multicyclic ring system. In one embodiment, the aryl group has 6-10 carbon atoms. The aryl is optionally substituted with at least one "ring system substituents" and combinations thereof as defined herein. Exemplary aryl groups include phenyl or naphthyl. An alkylaryl is an alkyl group as defined herein bonded to an aryl group as defined herein. The aryl group can be unsubstituted or substituted through available carbon atoms with one or more groups defined hereinabove for alkyl.

A "heteroaryl" group refers to a heteroaromatic system containing at least one heteroatom ring wherein the atom is selected from nitrogen, sulfur and oxygen. The heteroaryl contains 5 or more ring atoms. The heteroaryl group can be monocyclic, bicyclic, tricyclic and the like. Also included in this definition are the benzoheterocyclic rings. Non-limiting examples of heteroaryls include thienyl, benzothienyl, 1-naphthothienyl, thianthrenyl, furyl, benzofuryl, pyrrolyl, imidazolyl, pyrazolyl, pyridyl, pyrazinyl, pyrimidinyl, pyridazinyl, indolyl, isoindolyl, indazolyl, purinyl, isoquinolyl, quinolyl, naphthyridinyl, quinoxalinyl, quinazolinyl, cinnolinyl, pteridinyl, carbolinyl, thiazolyl, oxazolyl, isothiazolyl, isoxazolyl and the like. The heteroaryl group can be unsubstituted or substituted through available atoms with one or more groups defined hereinabove for alkyl.

A "heterocyclic ring" or "heterocyclyl" group refers to a five-membered to eight-membered rings that have 1 to 4 heteroatoms, such as oxygen, sulfur and/or in particular nitrogen. These five-membered to eight-membered rings can be saturated, fully unsaturated or partially unsaturated, with fully saturated rings being preferred. Preferred heterocyclic rings include piperidinyl, pyrrolidinyl pyrrolinyl, pyrazolinyl, pyrazolidinyl, morpholinyl, thiomorpholinyl, pyranyl, thiopyranyl, piperazinyl, indolinyl, dihydrofuranyl, tetrahydrofuranyl, dihydrothiophenyl, tetrahydrothiophenyl, dihydropyranyl, tetrahydropyranyl, and the like. An alkylheterocyclyl is an alkyl group as defined herein bonded to a heterocyclyl group as defined herein. The heterocyclyl group can be unsubstituted or substituted through available atoms with one or more groups defined hereinabove for alkyl.

"Ring system substituents" refer to substituents attached to aromatic or non-aromatic ring systems including, but not limited to, H, halo, haloalkyl, $(C_1\text{-}C_8)$alkyl, $(C_2\text{-}C_8)$alkenyl, $(C_2\text{-}C_8)$alkynyl, $(C_6\text{-}C_{10})$aryl, acyl, amido, ester, cyano, nitro, azido, and the like.

A "halogen" or "halo" group as used herein alone or as part of another group refers to chlorine, bromine, fluorine, and iodine. The term "haloalkyl" refers to an alkyl group having some or all of the hydrogens independently replaced by a halogen group including, but not limited to, trichloromethyl, tribromomethyl, trifluoromethyl, triiodomethyl, difluoromethyl, chlorodifluoromethyl, pentafluoroethyl, 1,1-difluoroethyl bromomethyl, chloromethyl, fluoromethyl, iodomethyl, and the like.

An "acyl" group as used herein encompasses groups such as, but not limited to, formyl, acetyl, propionyl, butyryl, pentanoyl, pivaloyl, hexanoyl, heptanoyl, octanoyl, nonanoyl, decanoyl, undecanoyl, dodecanoyl, benzoyl and the like. Currently preferred acyl groups are acetyl and benzoyl.

An "alkoxy" group refers to an —O-alkyl group wherein R is alkyl as defined above.

A "thio" group as used herein alone or as part of another group refers to an SH group. The terms "alkylthio", "arylthio" or "arylalkylthio" as used herein alone or as part of another group refer to any of the above alkyl, arylalkyl or aryl groups linked to a sulfur atom.

The terms "oligonucleotide" or "polynucleotide" as used herein refer to DNA or RNA of genomic or synthetic origin, which may be single- or double-stranded, and represent the sense or antisense strand.

The terms "peptide" and "protein" as used herein refer to a polymer of amino acid residues. The terms apply to amino acid polymers in which one or more amino acid residues is an artificial chemical analogue of a corresponding naturally occurring amino acid, as well as to naturally occurring amino acid polymers.

Many more molecules that satisfy the definition of "cubic NPCOCs" or "cubic nanoparticles capped with an organic coating" may be used in the same context.

According to certain embodiments, the sensors of the present invention are manufactured through a self-assembly process to produce films comprising cubic NPCOCs. The term "self-assembly" as used herein refers to a process of organization of molecules without intervening from an outside source. The self-assembly process takes place in a solution/solvent or directly on the solid-state substrate. The term "film", as used herein, corresponds to a configuration of well-arranged assembly of cubic NPCOCs, wherein each facet of a given cubic NPCOC is essentially in full contact with a facet of one of the other surrounding cubic NPCOCs. In this configuration, the fraction of voids between adjacent cubic nanoparticles is minimized (FIG. 1B). In contrast, the fraction of voids between adjacent spherical nanoparticles in films composed of SNPCOCs is significantly larger (FIG. 1A).

The synthesis of cubic NPCOCs is induced at the supersaturated regime along with selective adsorption of the capping agents (Lisiecki, *J. Phys. Chem. B*, 109, 12231, 2005). The synthesis can further be exemplified by either one of the following procedures:

i. Cubic platinum (Pt) nanoparticles capped with an organic coating are synthesized by bubbling hydrogen gas through an aqueous solution containing $K_2PtCl_4$ in the presence of the polymer used as capping material (El-Sayed et al., *Chem. Mater.*, 8, 1161, 1996).

ii. Cubic gold (Au) nanoparticles are grown using gentle reduction of the metal salt $HAuCl_4$ on a 3.5 nm gold seed used as a nucleation center. The process is performed with a large excess of a weak reducing agent (L-ascorbic acid) in the presence of a stabilizing agent (CTAB) according to Murphy et al. (*J. Am. Chem. Soc.* 126, 8648, 2004). In this manner, the growth of cubic nanoparticles is well-controlled resulting in nanoparticles with dimensions of approximately 50-60 nm. Smaller cubic nanoparticles are further synthesized through a modification of this procedure. The cubic nanoparticles synthesized by this procedure are fairly mono-disperse nanoparticles and are obtained in excellent yield.

According to the principles of the present invention, chemical sensing is produced by controlled aggregation and/or swelling of cubic NPCOCs as well as through changes in the permittivity constant of the nanoparticles' network, through various chemical interactions. The interactions include, but are not limited to, hydrogen-bonding, π-π, host-guest, van der Waals, electrostatic, charge-transfer, antigen-antibody interactions, and combinations thereof. The parameters that control aggregation and/or swelling include, but are not limited to, nanoparticles and/or aggregate size, inter-particle distance, composition, periodicity, and aggregate thermal stability. Changes in permittivity usually occurs in thin films having regions of discontinuities in chemiresistors, chemicapacitors and electrochemical cells which are composed of 2D or 3D films of metallic nanoparticles.

Exemplary methods for obtaining well-ordered two or three dimensional assemblies of cubic NPCOCs include, but are not limited to, i. Random deposition from solution of cubic NPCOCs on solid surfaces. The deposition is performed by drop casting, spin coating, spray coating and other similar techniques.

ii. Field-enhanced or molecular-interaction-induced deposition from solution of cubic NPCOCs on solid surfaces.

iii. Langmuir-Blodgett or Langmuir-Schaefer techniques. The substrate is vertically plunged through self-organized/well-ordered 2D monolayer of cubic NPCOCs at the air-subphase interface, wherein the latter being subsequently transferred onto it. Multiple plunging of the substrate through the 2D monolayer of cubic NPCOCs at the air-subphase interface, results in the fabrication of the 3D-ordered multilayers of cubic NPCOCs.

iv. Soft lithographic techniques, such as micro-contact printing (mCP), replica molding, micro-molding in capillaries (MIMIC), and micro-transfer molding (mTM). These methods are based on variations of self-assembly and replica molding of organic molecules and polymeric materials, for fabricating cubic NPCOCs from nanometer-scale to a mesoscopic scale (Whitesides et al., *J Mater. Chem.* 7, 1069, 1997).

v. Various combinations of Langmuir-Blodgett or Langmuir-Schaefer methods with soft lithographic techniques can be used to produce patterned Langmuir-Blodgett films of molecularly modified cubic NPCOCs which are transferred onto solid substrates.

vi. Printing on solid-state or flexible substrates using an inject printer designated for printed electronics. A solution containing the cubic NPCOCs is used as a filling material (or "ink") of the printing head according to procedures well known in the art as described in e.g. Holland et al. (*Ink Maker* 8, 83, 2005).

Assemblies/films of cubic NPCOCs can be used as an array of sensors in conjunction with learning and pattern recognition algorithms. Designing sensing-array elements have several advantages. The wide variety of ligands and synthetically-controlled structures provide the fabrication of chemically responsive yet distinctively different sensors. Through modifying the binding characters (e.g., non-covalent, hydrogen bonding, coordination, etc.) of the capping film and linker molecules, tunable molecular interactions and consequently enhanced selectivity can be achieved. Moreover, 3D assembly of the cubic structures provide controlled framework for signal amplifications. Coupling of nano-structures to solid substrates further provides easy array integration, rapid responses, and low power-driven portable devices.

In certain embodiments, the apparatus of the present invention comprises at least one sensor of cubic nanoparticles capped with an organic coating for the detection of specific volatile and non-volatile compounds. In particular embodiments, the apparatus of the present invention comprises an array of sensors of cubic nanoparticles capped with an organic coating. The array of sensors comprises a plurality of sensors between 2 to 1000 sensors, more preferably between 2 to 500 sensors, even more preferably between 2 to 250 sensors, and most preferably between 2 to 125 sensors in an array.

In some embodiments, the present invention provides sensing devices in which the cubic NPCOC sensors are used in conjunction with either one of a chemiresistor, chemicapacitor, quartz crystal microbalance, bulk acoustic wave (BAW) and surface acoustic wave (SAW) resonator, electrochemical cell, surface plasmon resonance (SPR), and optical spectroscopy.

According to the principles of the present invention, sensing responses upon exposure of the sensors to an analyte may be induced through a change in conductivity, resistance, impedance, capacitance, inductance, or optical properties of one or more of the sensors.

For electronically induced sensing, electrical contacts of the deposited films of cubic NPCOCs can be performed by methods well known in the art. Suitable methods include, but are not limited to, photolithography, e-beam lithography, Focused Ion Beam (FIB), direct evaporation/sputtering through shadow mask, soft (stamp) contact, inject printing techniques of conductive nanoparticles, and other similar techniques. Alternatively, films of nanoparticles can be deposited on ready-made contacts that were fabricated by the either one of the methods described hereinabove.

In currently preferred embodiments, sensing can be detected through changes in the optical properties a sensor network. In particular embodiments, sensing is carried out using spectroscopic ellipsometry. This technique measures the change in polarization upon reflection of polarized light from a surface. Without being bound by any theory or mechanism of action, the adsorption of analyte molecules induces changes in thickness of layers of cubic NPCOCs networks. The change in thickness or roughness induces changes in polarization which can be recorded by the spectroscopic ellipsometry technique. The signal obtained is subsequently conveyed to a learning and pattern recognition analyzer to generate a result. In this manner no electrical contacts are required. The aggregation and/or swelling of cubic NPCOCs upon analyte absorption render this technique advantageous for detecting volatile and non-volatile compounds with very high sensitivity.

Figure 2:
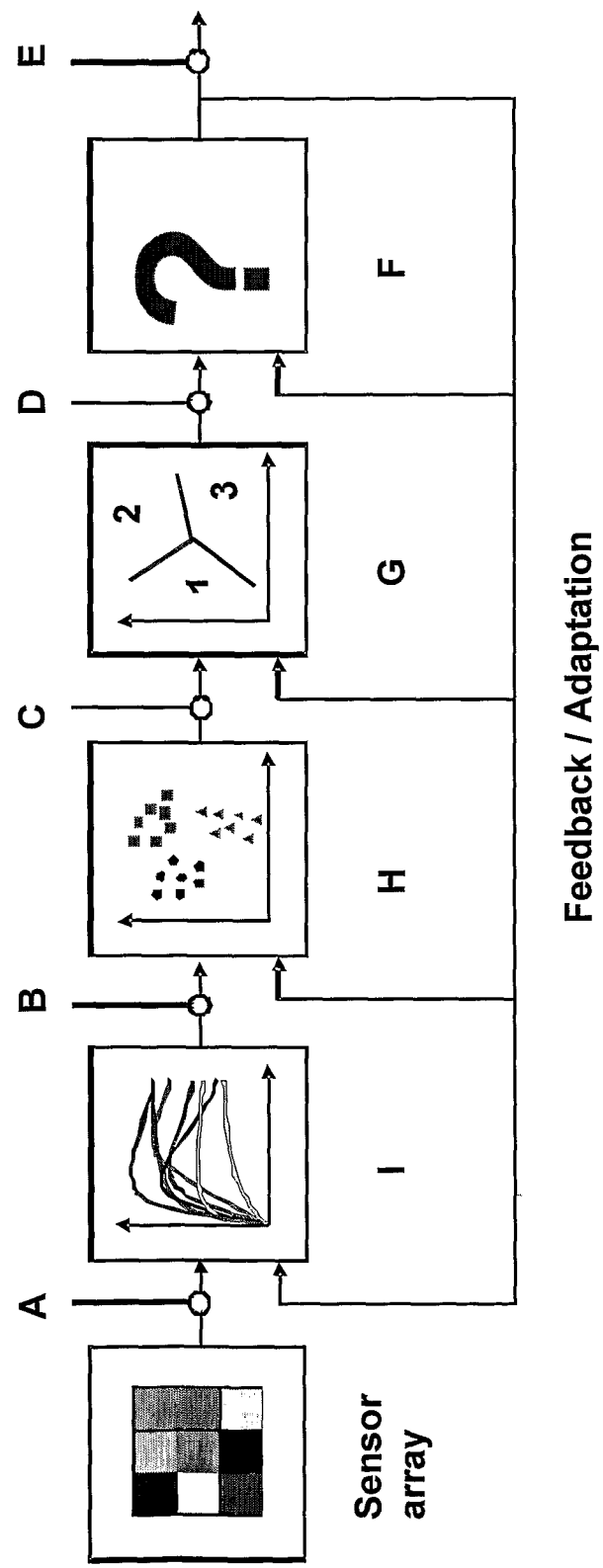
FIG. 2. A schematic diagram which illustrates the differentiation between odorants using an array of broadly-cross reactive sensors, in which each individual sensor responds to a variety of odorants, in conjugation with learning and pattern recognition algorithms to allow classification. 'A'—raw measurements, 'B'—normalized measurements, 'C'—feature vector, 'D'—odor class (confidence level), 'E'—post processed odor class, 'F'—decision making, 'G'—classification, 'H'—dimensionality reduction, and 'I'—signal preprocessing.

Within the scope of the present invention are methods for determining at least one of the composition and concentration of volatile and non-volatile compounds in a sample. The methods comprise exposing the sensors of cubic NPCOCs to a sample and using learning and pattern recognition algorithms in order to identify and possibly quantify desired compounds in a given sample. Thus, provided herein is a system comprising the apparatus of the present invention in conjunction with a learning and pattern recognition analyzer. The analyzer receives signal outputs or patterns from the apparatus and analyses them by various pattern recognition algorithms to produce an output signature. By sorting an unknown signature using a database of stored or known signatures, desired compounds can be identified. According to the principles of the present invention, sensing is obtained through adsorption of volatile and non-volatile compounds to provide signal changes which are then conveyed to a learning and pattern recognition analyzer to generate identification of desired compounds. FIG. 2 schematically illustrates the differentiation between odorants using the system of the present invention. Particularly, the array of sensors is exposed to a variety of volatile and non-volatile compounds to provide a response (either electronic or optical) vs. time ($2^{nd}$ box on the left). The dimensionality is then reduced wherein the data is represented by a new basis set ($f_2$ vs. $f_1$; $3^{rd}$ box on the left). This representation allows to classify the different odors (1, 2 & 3; $4^{th}$ box on the left). The procedure can be iteratively performed until satisfactory odor classification is achieved.

Algorithms for sample analysis, suitable for identifying and possibly quantifying volatile and non-volatile compounds include, but are not limited to, principal component analysis, Fischer linear analysis, neural network algorithms, genetic algorithms, fuzzy logic pattern recognition, and the like. After analysis is completed, the resulting information can, for example, be displayed on display, transmitted to a host computer, or stored on a storage device for subsequent retrieval.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes.

When a neural network is combined with a sensor array, the sensor data is propagated through the networks. In this manner, a series of vector matrix multiplications are performed and unknown analytes can be readily identified and determined. The neural network is trained by correcting the false or undesired outputs from a given input. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In some embodiments, the Fisher linear discriminant analysis (FLDA) and canonical discriminant analysis (CDA) as well as combinations thereof are used to compare the output signature and the available data from the database.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Principal component analysis compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common, but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

Methods and uses of the apparatus of the present invention in the fields of medicine, food quality control, and environmental monitoring are provided herein. In a currently preferred embodiment, the present invention provides a method for diagnosing a disease in a subject. The method is applicable for directly exposing the sensing apparatus to a sample of bodily fluid or secretion. Alternatively the sensing apparatus may be exposed to the headspace of a container wherein bodily fluids or secretions such as, but not limited to, serum, urine, feces, vaginal discharge, sperm, saliva, and the like have been deposited. The system is further applicable for detecting volatile and non-volatile compounds from breath directly exhaled by the subject on the apparatus, without a need for pre-concentrating or dehumidifying the sample. Other possibilities include exhaling into an inert bag and then exposing the collected breath to the apparatus of the present invention.

In a particular embodiment, the method described herein is used to diagnose cancer as well as to discriminate between different types of cancer. Gas-Chromatography linked with Mass-Spectrometry (GC-MS) studies have shown that volatile $C_4$-$C_{20}$ alkanes and certain monomethylated alkanes as well as benzene derivatives appear to be elevated in various instances of cancer. The compounds of interest are generally found in the range of 1-20 ppb in healthy human breath, but can be seen in distinctive mixture compositions at elevated levels in the range of 10-100 ppb in the breath of diseased patients. The levels of these biomarkers are elevated even at the early stages of the disease, since they reflect a change in human body chemistry. This change appears regardless of the cancerous tumor size. In addition, biomarkers of a specific disease (e.g., lung cancer) possess distinctive mixture compositions/patterns in comparison to biomarkers of other diseases even those of closely related diseases (e.g., breast cancer). Thus, using the methods of the present invention would allow the discrimination between different types of a similar disease.

In one embodiment, the present invention relates to the diagnosis of cancer using the apparatus/system disclosed herein. The term "cancer" refers to a disorder in which a population of cells has become, in varying degrees, unresponsive to the control mechanisms that normally govern proliferation and differentiation. Cancer refers to various types of malignant neoplasms and tumors, including primary tumors, and tumor metastasis. Non-limiting examples of cancers which can be detected by the apparatus and system of the present invention are brain, ovarian, colon, prostate, kidney, bladder, breast, lung, oral, and skin cancers. Specific examples of cancers are: carcinomas, sarcomas, myelomas, leukemias, lymphomas and mixed type tumors. Particular categories of tumors include lymphoproliferative disorders, breast cancer, ovarian cancer, prostate cancer, cervical cancer, endometrial cancer, bone cancer, liver cancer, stomach cancer, colon cancer, pancreatic cancer, cancer of the thyroid, head and neck cancer, cancer of the central nervous system, cancer of the peripheral nervous system, skin cancer, kidney cancer, as well as metastases of all the above. Particular types of tumors include hepatocellular carcinoma, hepatoma, hepatoblastoma, rhabdomyosarcoma, esophageal carcinoma, thyroid carcinoma, ganglioblastoma, fibrosarcoma, myxosarcoma, liposarcoma, chondrosarcoma, osteogenic sarcoma, chordoma, angiosarcoma, endotheliosarcoma, Ewing's tumor, leimyosarcoma, rhabdotheliosarcoma, invasive ductal carcinoma, papillary adenocarcinoma, melanoma, squamous cell carcinoma, basal cell carcinoma, adenocarcinoma (well differentiated, moderately differentiated, poorly differentiated or undifferentiated), renal cell carcinoma, hypernephroma, hypernephroid adenocarcinoma, bile duct carcinoma, choriocarcinoma, seminoma, embryonal carcinoma, Wilms' tumor, testicular tumor, lung carcinoma including small cell, non-small and large cell lung carcinoma, bladder carcinoma, glioma, astrocyoma, medulloblastoma, craniopharyngioma, ependymoma, pinealoma, retinoblastoma, neuroblastoma, colon carcinoma, rectal carcinoma, hematopoietic malignancies including all types of leukemia and lymphoma including: acute myelogenous leukemia, acute myelocytic leukemia, acute lymphocytic leukemia, chronic myelogenous leukemia, chronic lymphocytic leukemia, mast cell leukemia, multiple myeloma, myeloid lymphoma, Hodgkin's lymphoma, non-Hodgkin's lymphoma.

According to certain embodiments, the cancer to be diagnosed is selected from the group consisting of prostate cancer, breast cancer, skin cancer, colon cancer, lung cancer, pancreatic cancer, lymphoma, myeloma, leukemia, head and neck cancer, kidney cancer, ovarian cancer, bone cancer, liver cancer or thyroid cancer. According to exemplary embodiments, the cancer to be diagnosed is selected from breast cancer, kidney cancer, larynx cancer, vaginal tumor, stomach cancer, leukemia, including lymphoblastic leukemia, lung carcinoma, melanoma and colon cancer.

The system of the present invention can be utilized to diagnose other medical disorders including, but not limited to, acute asthma, hepatic encephalopathy, rheumatoid arthritis, renal failure, schizophrenia, ketosis, cardiopulmonary disease, uremia, diabetes mellitus, dysgeusia/dysosmia, cystinuria, cirrhosis, histidinemia, tyrosinemia, halitosis and phenylketonuria.

Due to the miniaturized dimensions of the apparatus (in the range of 10-100 nanometers to a few micrometers), it could be installed in any electronic device including, but not limited to, a watch or cellular phone. The integration of the apparatus to a commonly used electronic device allows it to be used as a warning system for the start of an infection or other disease in the body of an individual.

According to other embodiments, the apparatus/system of the present invention could be used for the detection of spoilage in food products via the determination of the composition and concentration of volatile and non-volatile compounds in a food sample. Information regarding early infectious and toxic agents can be gleaned using the apparatus of the present invention, in food production chains. According to another embodiment, the proposed technology could enable efficient warning of pollutions in water and air. These embodiments allow the use of the present invention for environmental monitoring.

Other aspects of the present invention include effective monitoring of pollution sources, namely, warning of pollution incidents, by-products, and wasted water; for detection of nitric oxide and sulfur dioxide in polluted air and car gas emission; for detection of spills in the chemical, pharmaceutical and biotechnology industries etc.

As used herein and in the appended claims the singular forms "a", "an," and "the" include plural references unless the content clearly dictates otherwise. Thus, for example, reference to "an organic coating" includes a plurality of such organic coatings and equivalents thereof known to those skilled in the art, and so forth.

The principles of the present invention are demonstrated by means of the following non-limitative examples.

EXAMPLES

Example 1

Production of Au Cubic Nanoparticles Capped with an Organic Coating (Cubic NPCOCs)

The synthesis of cubic nanoparticles having dimensions of approximately 25-35 nm (FIG. 3A) was performed using a modified seed-mediated growth procedure.

Specifically, gold seeds, having diameters of 1-3.5 nm, were synthesized using borohydride reduction of gold salt in the presence of CTAB as a capping agent. In a typical procedure, 0.25 ml of 0.01M $HAuCl_4*3H_2O$ solution was added to 7.5 ml of 0.1M CTAB solution. The solution was gently shaken, followed by the addition of 0.6 ml of an aqueous 0.01M $NaBH_4$ solution cooled down to ice temperatures, and rapid shaking for approximately 2 minutes. The solution was then stored at 25° C. for subsequent use.

Growth of cubic nanoparticles from Au seeds was performed by gentle reduction of the metal salt ($HAuCl_4$) on pre-prepared Au nucleation centers using a weak reducing agent (L-ascorbic acid) in the presence of a stabilizing agent, preferably CTAB. In particular, 0.2 ml of 0.01 M $HAuCl_4*3H_2O$ solution was added to a solution containing 8 ml of deionized water and 1.6 ml of 0.1M CTAB. The solution was gently mixed. Then, 0.95 ml of 0.1 M freshly prepared L-ascorbic acid solution was added. At this stage, the solution lost its orange color, indicating the reduction of $Au^{3+}$ to $Au^{1+}$. Further reduction of $Au^{1+}$ to $Au^0$ occurred upon mixing with 5 μl diluted (1:10) Au seed solution that was pre-aged for one hour. The growth medium was gently mixed and remained untouched for an hour or more. Finally, 1.5 ml of the solution was centrifuged for 15 minutes at 14,000 rpm to obtain the precipitate. The colorless supernatant was discarded. Rinsing of the precipitate was performed in 1.5 ml of deionized water followed by recentrifugation at 14,000 rpm. The precipitate was then redispersed in a suitable volume of deionized water depending on its quantity. This procedure provided cubic nanoparticles with more than 90% yield.

In order to obtain nanoparticles with reduced dimensions (in the range of 1-25 nm), gentle tuning of the gold seed to metal salt ($HAuCl_4$) ratio followed by rapid quenching of the gold precipitates at the early stages of the growth reaction was performed. In general, the procedure includes the following steps: fast centrifugation, fast cooling under −78° C., dilution with large volume of solvent and addition of quenching reagents.

The coating of synthesized cubic nanoparticles with organic molecules was performed as follows: the designated organic molecules were dispersed in solution at an overall concentration range of $10^{-5}$-$10^{-1}$ M, depending on the type and characteristics of the organic molecules. Adsorption of these molecules on the surfaces of the nanoparticles was performed by means of self-assembly.

Example 2

Characterization of Au Cubic Nanoparticles Capped with an Organic Coating (Cubic NPCOCs)

Figure 4:
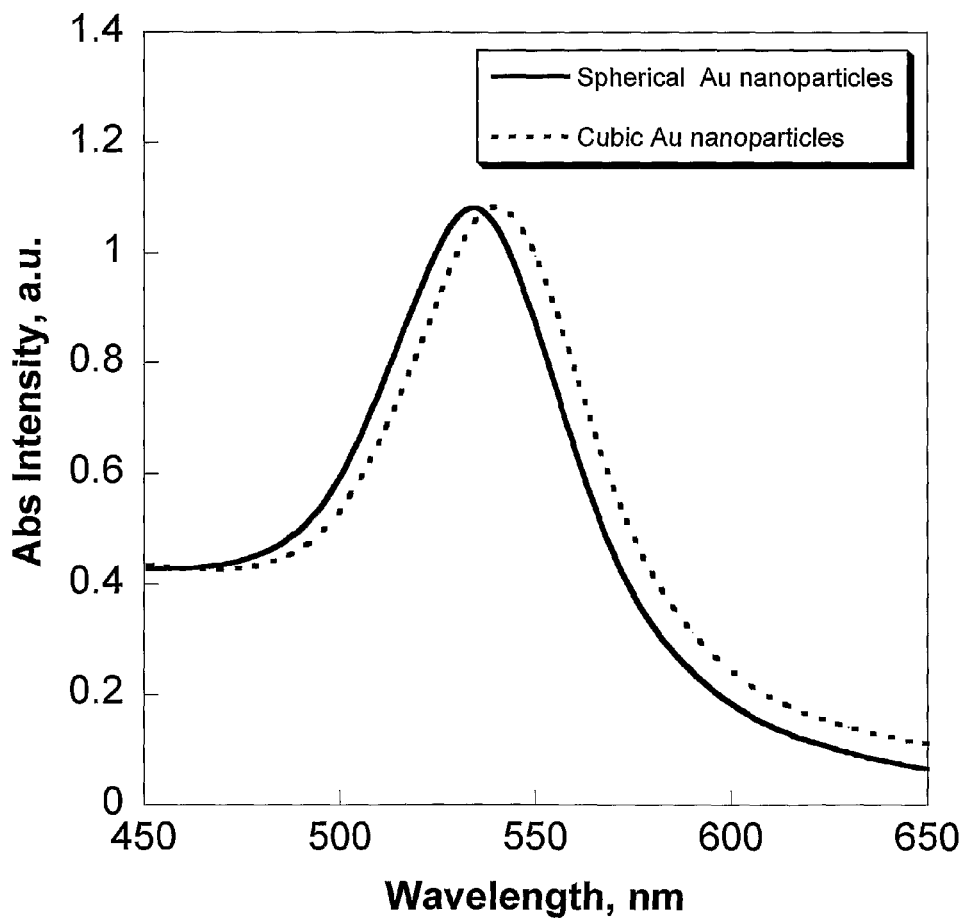
FIG. 4. Optical absorption spectra of solutions containing cubic (dotted line) and spherical (solid line) gold nanoparticles.

Transmission electron micrographs clearly show the cubic morphology of the gold nanoparticles of the present invention in comparison to the spherical nanoparticles (FIGS. 3A and 3B, respectively). The nanoparticles obtained were uniform in size and their dimensions ranged approximately between 25 to 35 nanometers. Optical absorption spectra of aqueous solutions containing 50 nm cubic and 25 nm spherical Au nanoparticles stabilized by bi-layer of CTAB surfactant are presented in FIG. 4 (dotted line and solid line, respectively). Nanoparticles possessing cubic morphology as well as nanoparticles possessing spherical morphology showed a single intense and sharp plasmon absorption band at approximately 535 nm. However, the plasmon absorption peak of the cubic Au nanoparticles was slightly red-shifted compared to that of the spherical ones. Without being bound by any theory or mechanism of action, this shift is attributed to the difference in nanoparticle size, wherein an increase in particle dimension positively correlates with a shift of the absorption band to longer wavelengths.

Example 3

Figure 5A:
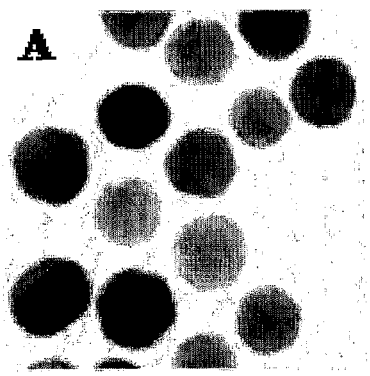
FIGS. 5A-5H. Transmission electron micrographs of gold nanoparticles precipitated from a solution dispersion after (5A) 1.5 minutes, (5B) 2.5 minutes, (5C) 3 minutes, (5D) 4 minutes, (5E) 6 minutes, (5F) 15 minutes, (5G) 1 hour, and (5H) overnight. Each micrograph represents a 110×110 $nm^2$ square.
Figure 5B:
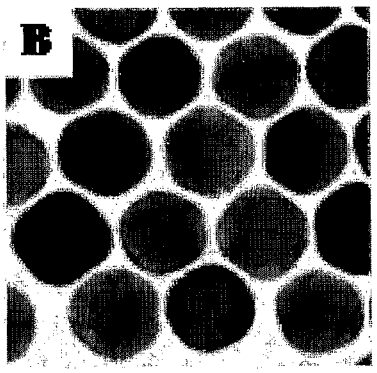
Figure 5C:
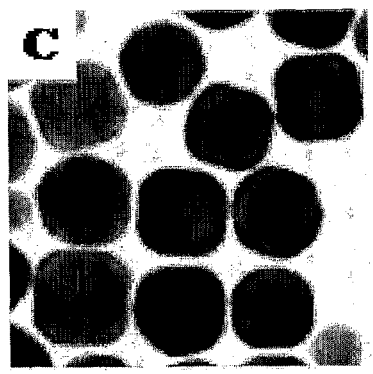
Figure 5D:
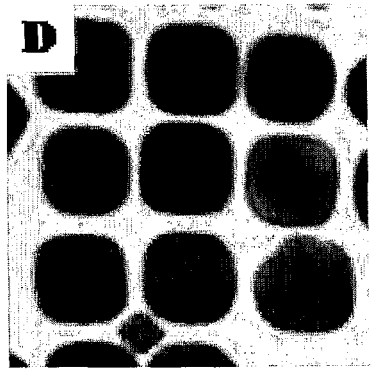

Morphology of the Au Cubic Nanoparticles Capped with an Organic Coating (Cubic NPCOCs) at Different Stages of Growth Au nanoparticles were quenched at different stages of the growth reaction and intermediate growth products were characterized (Haick & Dovgolevsky, Small, 4(11), 2059, 2008; published after the priority document U.S. 60/989,130). Structural and morphological analysis indicated that nanocubes are formed in the following shape transformation sequence: quasi-spherical shapes are transformed to decahedrons, to cuboctahedrons, and finally to nanocubes. FIGS. 5A-5H show transmission electron micrographs of Au nanoparticles growth products obtained at different quenching times. Au seeds that were grown for 1.5 minutes showed 17-23 nm quasi-spherical shapes (FIG. 5A). After a reaction time of 2.5 minutes, over 92% of the quasi-spherical nanoparticles kept their shape (approximate sizes 25-27 nm; FIG. 5B). The remaining Au nanoparticles (less than 8%) transformed to cubic-like shapes having edge length of 25-27 nm.

Figure 5E:
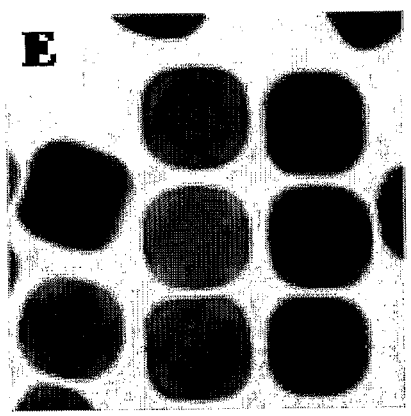
Figure 5F:
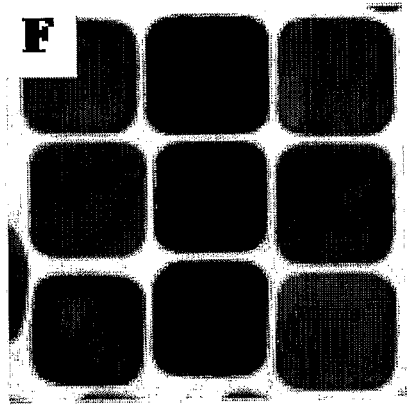
Figure 5G:
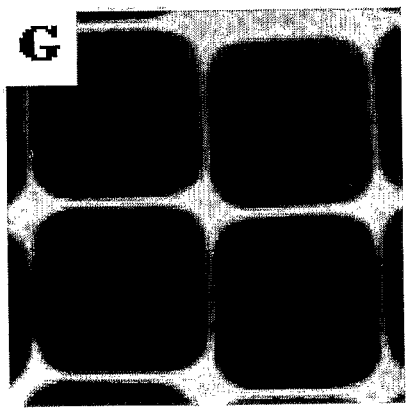
Figure 5H:
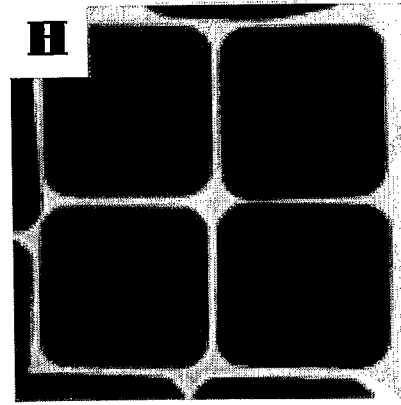

Increasing the reaction time to 3.0 and 4.0 minutes (FIGS. 5C and 5D, respectively) showed continuous disappearance of the quasi-spherical nanoparticles and evolution of further new nanocubes having 25-27 nm dimensions. Increasing the dispersion time from 6 to 15 to 60 minutes increased the size of the monodispersed nanocubes from 30±1 to 34±1 to 46±1 nm, respectively (FIGS. 5E, 5F and 5G). The nanocubes essentially ceased to grow after 24 hours dispersion time, yet they showed sharper corners than those grown at shorter dispersion times. These results were further confirmed based on similar shape transformation sequences for Pt, Pd, and Ag nanoparticles.

Example 4

Production of Sensors of Pt Cubic Nanoparticles Capped with an Organic Coating (Cubic NPCOCs)

Cubic and spherical (used for control) platinum nanoparticles stabilized by dodecanethiol (DDT) were obtained from pre-prepared polyacrylate- and polyvinylpyrrolidone-capped platinum nanoparticles, respectively. The DDT-capped platinum nanoparticles were prepared by ligand-exchanging of the original water-miscible stabilizing agents with water-immiscible dodecanethiol in a THF/water medium, accompanied by subsequent transformation of final dodecanethiol-capped nanoparticles into hydrophobic solvents (toluene or chloroform).

Cubic platinum nanoparticles (approximately 5 nm) stabilized with polyacrylate were synthesized in an aqueous solution from precursor platinum salt ($K_2PtCl_4$) in the presence of sodium polyacrylate (MW=21000; Aldrich) using $H_2$ reduction procedure (Narayanan & El-Sayed, *J. Phys. Chem. B*, 108, 5726, 2004). Control spherical platinum nanoparticles (approximately 5 nm) stabilized with polyvinylpyrrolidone (PVP, MW=40000; Aldrich) were synthesized in ethanol solution from precursor platinum salt $K_2PtCl_4$ at approximately 90° C. under reflux (Narayanan & El-Sayed, *J. Phys. Chem. B*, 107, 12416, 2003).

Chemical sensors based on platinum nanoparticle films were prepared by drop casting deposition from toluene solution on interdigitated microsensor electrode (IME, ABTECH) devices. IME devices, composed of 25 pairs of gold electrodes having 20 μm width and separated each by 20 μm spacing on a glass substrate, were used. A computer-interfaced multi-channel device analzyer was used to measure the lateral resistance of platinum nanoparticle films on IME upon exposure to different analyte vapors. Vapors were introduced by bubbling air gas through the different analytes in liquid state. The partial pressures of analyte vapors varied between 0.05 and 0.08 $p/p_0$. All analytes were purchased from Aldrich.

Example 5

Electrical Resistance Upon Exposure to Different Analytes

Pt cubic vs. spherical NPCOC films on interdigitated microsensor electrode, that were prepared according to example 4, were measured for their electrical responses upon exposure to different analyte vapors. While electrical resistance of nanoparticle films was directly measured, the relative differential electrical resistance $\Delta R/R_i$ (where $R_i$ is the initial resistance of the nanoparticle film in the absence of analyte and $\Delta R$ is the change of resistance upon exposure to analyte relative to the initial resistance $R_i$) was calculated in order to assess the sensor response signal.

Vapor analytes used for assessing sensing performances where chosen to include compounds having different chemical and physical properties including structure, size of molecule, hydrophobicity and inter-molecular interactions with the capping agent of the nanoparticles. Undecane, octane and hexane were chosen as hydrophobic molecules with zero dipole moments, whereas ethanol (D=1.69 DB) and trichloroethane (D=0.8 DB) where chosen as organic hydrophilic molecules with high and medium dipole moments, respectively. The initial resistances for cubic and spherical Pt nanoparticles capped with dodecanethiol films on IME devices in the absence of analyte vapors were determined as 0.44 and 0.35 Mega-Ohm, respectively.

Figure 6:
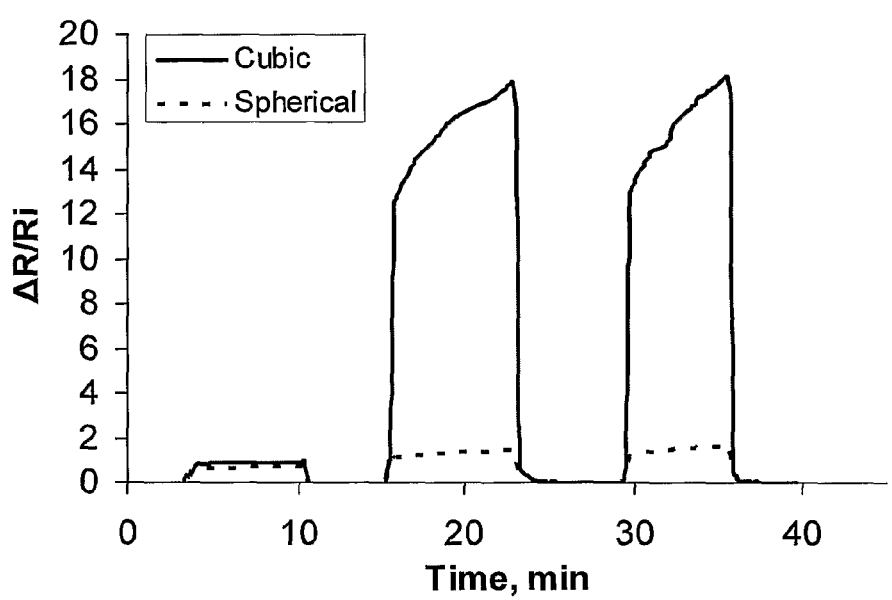
FIG. 6. Sensor response of cubic (solid line) and spherical (dotted line) DDT-capped platinum nanoparticles upon exposure to undecane vapor.
Figure 7:
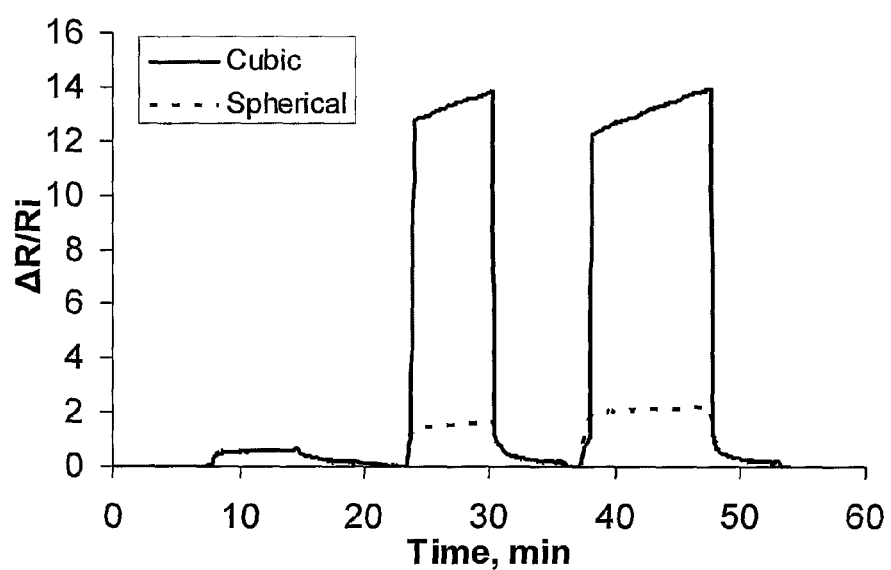
FIG. 7. Sensor response of cubic (solid line) and spherical (dotted line) DDT-capped platinum nanoparticles upon exposure to octane vapor.
Figure 8:
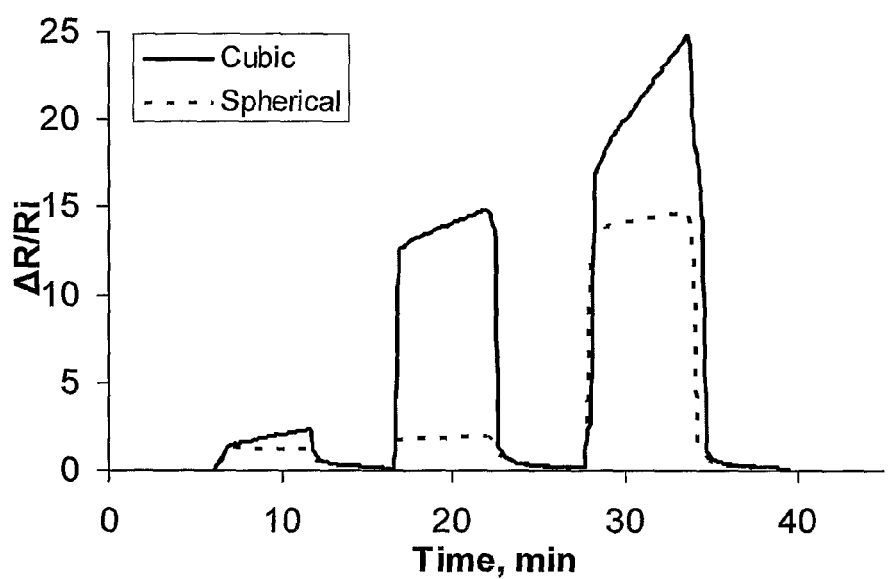
FIG. 8. Sensor response of cubic (solid line) and spherical (dotted line) DDT-capped platinum nanoparticles upon exposure to hexane vapor.
Figure 9:
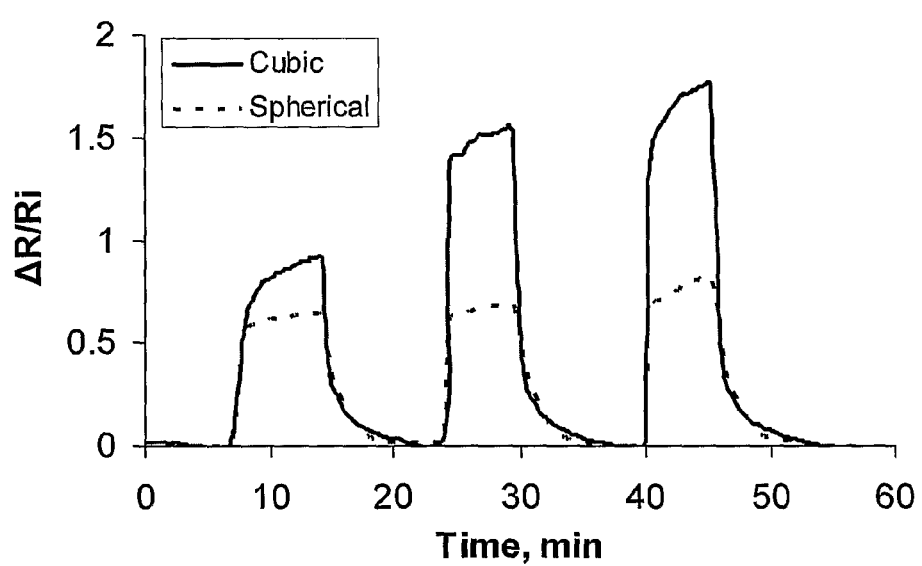
FIG. 9. Sensor response of cubic (solid line) and spherical (dotted line) DDT-capped platinum nanoparticles upon exposure to ethanol vapor.
Figure 10:
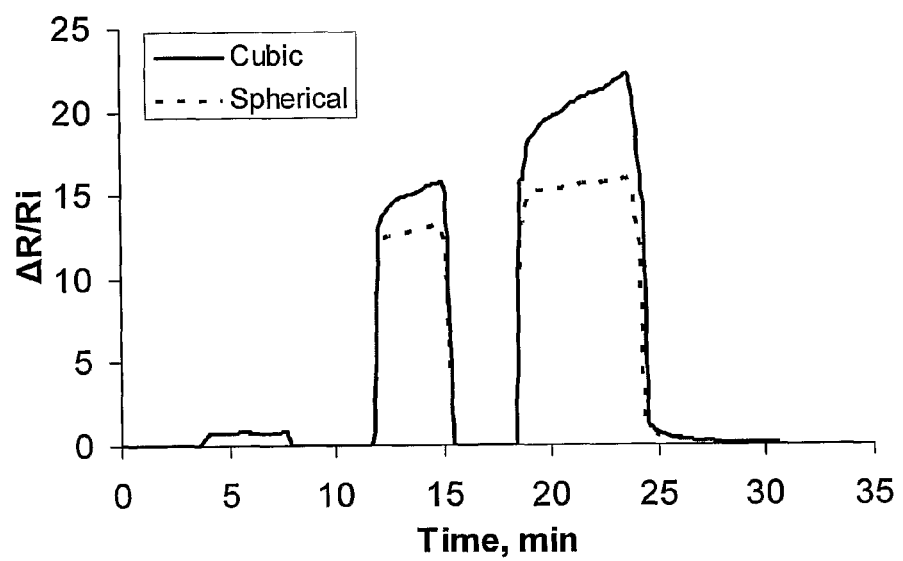
FIG. 10. Sensor response of cubic (solid line) and spherical (dotted line) DDT-capped platinum nanoparticles upon exposure to trichloroethane vapor.

FIGS. 6-10 show sensor response ($\Delta R/R_i$) of cubic (solid lines) and spherical (dotted lines) nanoparticles capped with dodecanethiol to various analyte vapors. FIG. 6 shows the sensor response upon exposure to 0.026 ppm (left), 0.030 ppm (middle), and 0.032 ppm (right) of undecane vapor. FIG. 7 shows the sensor response upon exposure to 0.68 ppm (left), 0.80 ppm (middle), and 0.84 ppm (right) of octane vapor. FIG. 8 shows the sensor response upon exposure to 7.96 ppm (left), 9.29 ppm (middle), and 9.80 ppm (right) of hexane vapor. FIG. 9 shows the sensor response upon exposure to 2.89 ppm (left), 3.37 ppm (middle), and 3.55 ppm (right) of ethanol vapor. FIG. 10 shows the sensor response upon exposure to 3.80 ppm (left), 4.44 ppm (middle), and 4.68 ppm (right) of trichloroethane vapor.

As shown from the sensor response profile of both NPCOC films, all analytes produced rapid responses of the sensors. Additionally the responses were fully reversible while purging reference gas. Table 1 summarizes sensor response values of cubic vs. spherical NPCOCs upon exposure to different analyte vapors.

TABLE 1

Sensor response of Cubic vs. Spherical Pt nanoparticles capped with dodecanethiol upon exposure to different concentrations $(p/p_0)$* of different analyte vapors.

| Analyte/ Sensor | Undecane [D] = 0 | | | Octane [D] = 0 | | | Hexane [D] = 0 | | | Trichloroethane [D] = 1.4 | | | Ethanol [D] = 1.69 | | |
|---|---|---|---|---|---|---|---|---|---|---|---|---|---|---|---|
| | 0.05 | 0.07 | 0.08 | 0.05 | 0.07 | 0.08 | 0.05 | 0.07 | 0.08 | 0.05 | 0.07 | 0.08 | 0.05 | 0.07 | 0.08 |
| Cubic | 0.92 | 17.9 | 28.0 | 0.64 | 13.8 | 24.0 | 1.76 | 14.8 | 24.8 | 1.11 | 15.8 | 23.2 | 0.92 | 1.56 | 2.76 |
| Spherical | 0.11 | 1.44 | 2.68 | 0.13 | 1.64 | 2.17 | 0.22 | 2.00 | 14.7 | 0.14 | 13.2 | 15.9 | 0.14 | 0.29 | 0.82 |

*0.05, 0.07 and 0.08 $p/p_0$ of different analyte vapors correspond to their following concentrations: 0.026 ppm, 0.030 ppm and 0.032 ppm for undecane; 0.68 ppm, 0.80 ppm and 0.84 ppm for octane; 7.96 ppm, 9.29 ppm and 9.80 ppm for hexane; 2.89 ppm, 3.37 ppm and 3.55 ppm for ethanol; and 3.80 ppm, 4.44 ppm and 4.68 ppm of trichloroethane.

A comparison of the electronic responses of cubic vs. spherical NPCOCs shows unequivocally the advantage of cubic NPCOCs in comparison to SNPCOCs. The data clearly shows that the sensor response of cubic Pt nanoparticles is significantly larger than that of spherical Pt nanoparticles, independently on the type of analyte used. The increased sensitivity of cubic nanoparticles compared to spherical nanoparticles is even more pronounced at increased flow rates to produce values which are more than 11 times the response of SNPCOCs.

Additionally, hydrophobicity of the analyte molecules as well as their size play a significant role in sensor responses. It is evident that the sensor response to hydrophobic analytes was higher than the response to hydrophilic analytes. Without being bound by any theory or mechanism of action, this behavior is attributed to the chemical similarity of the hydrophobic capping agent—dodecanethiol with the hydrophobic analytes which introduces a more pronounced effect. Thus, fine tuning of the capping agent to the analyte to be detected yields better sensing signals. It is further denoted that the sensitivity was improved for alkanes having longer chains (undecane vs. hexane), whereas the shorter alkanes introduced a sharp increase in sensor response at higher flow rates. Without being bound by any theory or mechanism of action, the increased sensitivity for longer alkanes might be attributed to increased swelling/aggregation of the capping molecules by longer alkane molecules. The sharp response observed for shorter alkanes might be attributed to easier penetration of shorter alkane molecules to deeper layers of nanoparticle films.

The results presented herein clearly show that cubic NPCOC sensors exhibit significantly higher sensitivity towards different types of analytes in comparison to SNP-COC sensors. The data further teaches that the organic capping molecules can be chosen at will to provide improved sensitivities for particular analyte molecules. An apparatus which comprises an array of chemically sensitive cubic NPCOC sensors can thus be designed for maximizing the physical and chemical interactions between capping agent and different analyte molecules.

Example 6

Relative Change in Film Thickness Upon Exposure to Different Analytes

The relative changes of thicknesses of cubic vs. spherical nanoparticle films was studied using spectroscopic ellipsometry. In particular, undecane, octane and hexane vapors at different partial pressures ($p/p_0$) were used as analytes in order to determine the sensitivity of cubic NPCOCs in comparison to SNPCOC thin films.

Relative thickness changes of the nanoparticle films at different partial pressures of the analyte vapor, were calculated as $\Delta d/d_i$, wherein $\Delta d$ and $d_i$ correspond to differential thickness and initial film thickness, respectively. Cubic and spherical Pt nanoparticle films were deposited on $p^{++}Si(100)/SiO_2$ substrates by drop casting from toluene solution. The samples were mounted in a closed exposure cell onto the sample stage of the ellipsometer and exposed to analyte vapors (undecane, octane and hexane) carried by dry air at partial pressure ($p/p_0$) ranging between 0.05 and 0.08 at ambient conditions (24° C.). Ellipsometric spectra were recorded every 2 minutes at an incidence angle of 70°. The spectra were recorded over a spectral rage of 245 to 1700 nm, using a Woollam M2000U ellipsometer equipped with a CCD camera for fast recording.

Table 2 summarizes the thickness changes of cubic vs. spherical NPCOC films upon exposure to different analyte vapors. Values of corresponding effective relative changes in film thickness normalized according to the extent of voids between nanoparticles after analyte sorption in cubic (0.1%) and spherical (0.6%) NPCOC array are incorporated as well. The data represented herein shows that an increase in thickness of both nanoparticle films occurred upon analyte exposure. Furthermore, the thickness of both nanoparticle films increased upon increasing the partial pressure of the analyte. However, the cubic nanoparticle array produced a significantly enhanced signal in comparison to the spherical nanoparticle array. Changes in film thickness upon exposure to analyte vapors were more pronounced in cubic NPCOC films as compared to SNPCOC films. The relative change in thickness of cubic nanoparticle film upon exposure to 0.05 $p/p_0$ undecane was one-fold larger than the relative change in thickness of spherical nanoparticle film. The corresponding effective relative change of thickness normalized according to the extent of voids between nanoparticles after undecane sorption produced a result which is two-fold larger for cubic NPCOC films in comparison to spherical NPCOC films. The increased signal in cubic NPCOC was further exemplified using hexane and octane. Without being bound by any theory or mechanism of action, these analyte molecules having shorter chain lengths as compared to undecane, induced more pronounced changes which may be attributed to their ability to penetrate deeper into the film thus introducing enhanced increase in thickness.

TABLE 2

Relative changes in thickness ($\Delta d/d_i$) and the corresponding effective relative changes in thickness ($\Delta d/(d_i * \% V)$) of cubic and spherical nanoparticle films upon exposure to different analyte vapors at different partial pressures.

| Analyte/ Sensor | $p/p_0$ | Cubic NP | | Spherical NP | |
|---|---|---|---|---|---|
| | | $\Delta d/d_i$ | $\Delta d/(d_i * \%V)$ | $\Delta d/d_i$ | $\Delta d/(d_i * \%V)$ |
| undecane | 0.05 | 7.2 | 71.6 | 0.8 | 0.5 |
| undecane | 0.08 | 15.7 | 157.2 | 1.4 | 0.9 |
| octane | 0.05 | 34.7 | 347.1 | 5.5 | 3.3 |
| octane | 0.01 | 27.7 | 277.6 | 4.2 | 2.5 |
| hexane | 0.05 | 32.4 | 324.1 | 6.1 | 3.7 |
| hexane | 0.01 | 20.1 | 200.9 | 4.2 | 2.5 |

Hence it is clearly shown that cubic nanoparticle films produce a more pronounced optical as well as electrical response upon exposure to different analyte vapors in comparison to spherical nanoparticle films, independently of the type of analyte used. Cubic NPCOC sensors are therefore more sensitive towards different analyte vapors in comparison to SNPCOC sensors.

It is appreciated by persons skilled in the art that the present invention is not limited by what has been particularly shown and described hereinabove. Rather the scope of the present invention includes both combinations and sub-combinations of various features described hereinabove as well as variations and modifications. Therefore, the invention is not to be construed as restricted to the particularly described embodiments, and the scope and concept of the invention will be more readily understood by references to the claims, which follow.

The invention claimed is:
1. A system having:
(i) an apparatus comprising an array of chemically sensitive sensors comprising a plurality of cubic nanoparticle conductive cores, comprising six facets and capped with an organic coating, wherein the cubic nanoparticle conductive cores capped with an organic coating are ordered in a configuration selected from 1D wires, 2D films and 3D assemblies having minimized voids and essentially full interface contacts between adjacent facets of the cubic nanoparticle conductive cores capped with an organic coating, wherein the chemically sensitive sensors detect volatile and non-volatile compounds through swelling or aggregation of the cubic nanoparticles upon analyte adsorption thereon; and (ii) a learning and pattern recognition analyzer, wherein said learning and pattern recognition analyzer receives sensor output signals and compares them to stored data.

2. The system according to claim 1, wherein the cubic nanoparticle conductive cores are capped with an organic coating comprising a monolayer or multilayers of organic compounds, wherein the organic compounds are selected from small molecules, monomers, oligomers and polymers.

3. The system according to claim 1, wherein the cubic nanoparticle conductive cores are selected from the group consisting of Au, Ag, Ni, Co, Pt, Pd, Cu, Al, Au/Ag, Au/Cu, Au/Ag/Cu, Au/Pt, Au/Pd, Au/Ag/Cu/Pd, Pt/Rh, Ni/Co, and Pt/Ni/Fe.

4. The system according to claim 1, wherein the organic coating is selected from the group consisting of alkylthiols with $C_3$-$C_{24}$ chains, ω-functionalized alkanethiolates, arenethiolate, (γ-mercaptopropyl)tri-methyloxysilane, dialkyl disulfides, xanthates, oligonucleotides, polynucleotides, peptides, proteins, enzymes, polysaccharides, phospholipids, and combinations thereof.

5. The system according to claim 1, further comprising at least one of a chemiresistor, chemicapacitor, quartz crystal microbalance, bulk acoustic wave (BAW) and surface acoustic wave (SAW) resonator, electrochemical cell, surface plasmon resonance (SPR), and optical spectroscope.

6. The system according to claim 1, wherein the learning and pattern recognition analyzer comprises at least one algorithm selected from the group consisting of artificial neural network algorithms, principal component analysis (PCA), multi-layer perception (MLP), generalized regression neural network (GRNN), fuzzy inference systems (FIS), self-organizing map (SOM), radial bias function (RBF), genetic algorithms (GAS), neuro-fuzzy systems (NFS), adaptive resonance theory (ART), partial least squares (PLS), multiple linear regression (MLR), principal component regression (PCR), discriminant function analysis (DFA), linear discriminant analysis (LDA), cluster analysis, and nearest neighbor.

7. A method for determining at least one of the composition and concentration of selected volatile and non-volatile compounds in a sample, comprising the steps of:

(i) providing a system comprising an apparatus comprising an array of chemically sensitive sensors comprising a plurality of cubic nanoparticle conductive cores, comprising six facets and capped with an organic coating, wherein the cubic nanoparticle conductive cores capped with an organic coating are ordered in a configuration selected from 1D wires, 2D films and 3D assemblies having minimized voids and essentially full interface contacts between adjacent facets of the cubic nanoparticle conductive cores capped with an organic coating, wherein the chemically sensitive sensors detect volatile and non-volatile compounds through swelling or aggregation of the cubic nanoparticles upon analyte adsorption thereon, and a learning and pattern recognition analyzer, wherein the learning and pattern recognition analyzer receives sensor output signals and compares them to stored data;

(ii) exposing the sensor array of the apparatus to the sample; and (iii) using pattern recognition algorithms to detect the presence of volatile and non-volatile compounds in the sample.

8. The method according to claim 7, for detecting volatile and non-volatile compounds indicative of a disease in a subject.

9. The method according to claim 8, wherein the disease is selected from the group consisting of cancer, acute asthma, hepatic encephalopathy, rheumatoid arthritis, renal failure, schizophrenia, ketosis, cardiopulmonary disease, uremia, diabetes mellitus, dysgeusia/dysosmia, cystinuria, cirrhosis, histidinemia, tyrosinemia, halitosis and phenylketonuria.

10. The method according to claim 8, for differentiating between different types of cancer.

11. The method according to claim 8, wherein the sample comprises at least one bodily fluid or secretion selected from the group consisting of serum, urine, feces, sweat, vaginal discharge, saliva, and sperm.

12. The method according to claim 7, for detecting volatile and non-volatile compounds indicative of spoilage in food products.

13. The method according to claim 7, for detecting volatile and non-volatile compounds indicative of environmental pollution.

14. The method according to claim 7 comprising measuring a response selected from an electronic response and optical response.

15. An apparatus comprising: an array of chemically sensitive sensors comprising a plurality of cubic nanoparticle conductive cores, comprising six facets and capped with an organic coating, wherein the cubic nanoparticle conductive cores capped with an organic coating are ordered in a configuration selected from 1D wires, 2D films and 3D assemblies having minimized voids and essentially full interface contacts between adjacent facets of the cubic nanoparticle conductive cores capped with an organic coating, wherein the chemically sensitive sensors detect volatile and non-volatile compounds with sensitivity of less than one part per million (ppm) through swelling or aggregation of the cubic nanoparticles upon analyte adsorption thereon.

16. The apparatus according to claim 15, wherein the cubic nanoparticle conductive cores are capped with an organic coating comprising a monolayer or multilayers of organic compounds, wherein the organic compounds are selected from small molecules, monomers, oligomers and polymers.

17. The apparatus according to claim 15, wherein the cubic nanoparticle conductive cores are selected from the group consisting of Au, Ag, Ni, Co, Pt, Pd, Cu, Al, Au/Ag, Au/Cu, Au/Ag/Cu, Au/Pt, Au/Pd, Au/Ag/Cu/Pd, Pt/Rh, Ni/Co, and Pt/Ni/Fe.

18. The apparatus according to claim 15, wherein the organic coating is selected from the group consisting of alkylthiols with $C_3$-$C_{24}$ chains, ω-functionalized alkanethiolates, arenethiolate, (γ-mercaptopropyl)tri-methyloxysilane, dialkyl disulfides, xanthates, oligonucleotides, polynucleotides, peptides, proteins, enzymes, polysaccharides, phospholipids, and combinations thereof.

19. The apparatus according to claim 15, further comprising at least one of a chemiresistor, chemicapacitor, quartz crystal microbalance, bulk acoustic wave (BAW) and surface acoustic wave (SAW) resonator, electrochemical cell, surface plasmon resonance (SPR), and optical spectroscope.

* * * * *